US008535290B2

(12) United States Patent
Evans et al.

(10) Patent No.: US 8,535,290 B2
(45) Date of Patent: Sep. 17, 2013

(54) APPARATUS AND METHODS FOR CLOT DISSOLUTION

(75) Inventors: Michael A. Evans, Palo Alto, CA (US); Denise Demarais, Los Gatos, CA (US); Dino De Cicco, Campbell, CA (US); Kelvin Ning, Palo Alto, CA (US); Alexander Khairkhahan, Palo Alto, CA (US); Tyler Jon Strang, Palo Alto, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/548,338

(22) Filed: Jul. 13, 2012

(65) Prior Publication Data

US 2012/0283699 A1 Nov. 8, 2012

Related U.S. Application Data

(60) Division of application No. 12/816,347, filed on Jun. 15, 2010, now Pat. No. 8,241,241, which is a continuation of application No. 10/142,005, filed on May 8, 2002, now Pat. No. 7,763,010, which is a continuation-in-part of application No. 09/491,401, filed on Jan. 25, 2000, now Pat. No. 6,663,613, and a continuation-in-part of application No. PCT/US01/02406, filed on Jan. 24, 2001.

(51) Int. Cl.
*A61M 31/00* (2006.01)
(52) U.S. Cl.
USPC ......... 604/508; 604/22; 604/101.01; 604/509
(58) Field of Classification Search
USPC ............. 604/22, 96.01, 101.01, 101.05, 508, 604/509; 606/128
See application file for complete search history.

(56) References Cited

U.S. PATENT DOCUMENTS

| 4,425,908 A | 1/1984 | Simon |
| 4,445,509 A | 5/1984 | Auth |

(Continued)

FOREIGN PATENT DOCUMENTS

| EP | 0501772 | 9/1992 |
| WO | WO 96/01591 | 1/1996 |

(Continued)

OTHER PUBLICATIONS

Bildsoe et al., "Mechanical Clot Dissolution: New Concept," Radiology, vol. 171, No. 1, pp. 231-233 (Apr. 1989).

(Continued)

*Primary Examiner* — Theodore Stigell
(74) *Attorney, Agent, or Firm* — Thomas M. Johnston, Esq.

(57) ABSTRACT

Clot disruption and dissolution are achieved using a catheter having the ability to infuse a thrombolytic agent, aspirate clot and fluid, and allow passage of a guidewire. Optionally, the catheter may also include a mechanical agitator for further disrupt clot in the presence of the thrombolytic agent. A flow resistor in the catheter provides for infusion and/or aspiration to be concentrated primarily at a clot treatment area in a blood vessel while also providing optional infusion and/or aspiration distal to the treatment area. In some embodiments, infusion, aspiration and guidewire passage occur through a common lumen. The thrombolytic agent, such as tPA, streptokinase, or urokinase, is directly released into the clot at the point where the agitator is engaging the clot. In this way, the thrombolytic activity of the agent is enhanced and the dissolution of the clot is improved.

13 Claims, 24 Drawing Sheets

(56) References Cited

U.S. PATENT DOCUMENTS

| | | |
|---|---|---|
| 4,573,966 A | 3/1986 | Weikl et al. |
| 4,646,736 A | 3/1987 | Auth |
| 4,794,928 A | 1/1989 | Kletschka |
| 4,923,462 A | 5/1990 | Stevens |
| 5,041,093 A | 8/1991 | Chu |
| 5,059,178 A | 10/1991 | Ya |
| 5,067,957 A | 11/1991 | Jervis |
| 5,116,352 A | 5/1992 | Schnepp-Pesch et al. |
| 5,135,484 A | 8/1992 | Wright |
| 5,163,905 A | 11/1992 | Don Michael |
| 5,176,693 A | 1/1993 | Pannek, Jr. |
| 5,190,546 A | 3/1993 | Jervis |
| 5,222,941 A | 6/1993 | Don Michael |
| 5,279,546 A | 1/1994 | Mische et al. |
| 5,284,486 A | 2/1994 | Kotula et al. |
| 5,304,115 A * | 4/1994 | Pflueger et al. ........... 604/22 |
| 5,312,427 A | 5/1994 | Shturman |
| 5,330,484 A | 7/1994 | Günther et al. |
| 5,356,418 A | 10/1994 | Shturman |
| 5,360,432 A | 11/1994 | Shturman |
| 5,370,653 A | 12/1994 | Cragg |
| 5,380,273 A | 1/1995 | Dubrul et al. |
| 5,410,093 A | 4/1995 | Dorai |
| 5,417,703 A | 5/1995 | Brown et al. |
| 5,419,774 A | 5/1995 | Willard et al. |
| 5,462,529 A * | 10/1995 | Simpson et al. ........ 604/101.04 |
| 5,490,859 A | 2/1996 | Mische et al. |
| 5,498,236 A | 3/1996 | Dubrul et al. |
| 5,501,694 A | 3/1996 | Ressemann et al. |
| 5,507,795 A | 4/1996 | Chiang et al. |
| 5,540,707 A | 7/1996 | Ressemann et al. |
| 5,549,119 A | 8/1996 | Solar |
| 5,554,114 A | 9/1996 | Wallace et al. |
| 5,554,163 A | 9/1996 | Shturman |
| 5,556,408 A | 9/1996 | Farhat |
| 5,569,275 A | 10/1996 | Kotula et al. |
| 5,584,843 A | 12/1996 | Wulfman et al. |
| 5,630,823 A | 5/1997 | Schmitz-Rode et al. |
| 5,643,228 A | 7/1997 | Schucart et al. |
| 5,674,198 A | 10/1997 | Leone |
| 5,709,874 A | 1/1998 | Hanson et al. |
| 5,713,848 A | 2/1998 | Dubrul et al. |
| 5,758,656 A | 6/1998 | Schroeder |
| 5,766,191 A | 6/1998 | Trerotola |
| 5,795,322 A | 8/1998 | Boudewijn |
| 5,836,868 A | 11/1998 | Ressemann et al. |
| 5,843,103 A | 12/1998 | Wulfman |
| 5,873,882 A | 2/1999 | Straub et al. |
| 5,876,414 A | 3/1999 | Straub |
| 5,897,567 A | 4/1999 | Ressemann et al. |
| 5,904,698 A | 5/1999 | Thomas et al. |
| 5,908,395 A | 6/1999 | Stalker et al. |
| 5,928,203 A | 7/1999 | Davey et al. |
| 5,947,985 A | 9/1999 | Imran |
| 5,951,514 A | 9/1999 | Sahota |
| 5,954,737 A | 9/1999 | Lee |
| 5,957,901 A | 9/1999 | Mottola et al. |
| 5,972,019 A | 10/1999 | Engelson et al. |
| 6,022,336 A | 2/2000 | Zadno-Azizi et al. |
| 6,027,514 A | 2/2000 | Stine et al. |
| 6,036,708 A | 3/2000 | Sciver |
| 6,063,069 A | 5/2000 | Cragg et al. |
| 6,090,118 A | 7/2000 | McGuckin, Jr. |
| 6,113,614 A | 9/2000 | Mears |
| 6,146,395 A | 11/2000 | Kanz et al. |
| 6,156,046 A | 12/2000 | Passafaro et al. |
| 6,168,579 B1 | 1/2001 | Tsugita |
| 6,179,816 B1 | 1/2001 | Mottola et al. |
| 6,295,990 B1 | 10/2001 | Lewis et al. |
| 6,306,124 B1 | 10/2001 | Jones et al. |
| 6,322,572 B1 | 11/2001 | Lee |
| 6,383,205 B1 | 5/2002 | Samson et al. |
| 6,485,500 B1 | 11/2002 | Kokish et al. |
| 6,682,499 B2 | 1/2004 | Lenker |
| 2002/0188276 A1 | 12/2002 | Evans et al. |

FOREIGN PATENT DOCUMENTS

| | | |
|---|---|---|
| WO | WO 96/29941 | 10/1996 |
| WO | WO 97/11738 | 4/1997 |
| WO | WO 98/38926 | 9/1998 |
| WO | WO 99/04701 | 2/1999 |
| WO | WO 99/23952 | 5/1999 |
| WO | WO 00/41762 | 7/2000 |
| WO | WO 01/54754 | 8/2001 |

OTHER PUBLICATIONS

Kandarpa et al., "Forceful Pulsatile Local Infusion of Enzyme Accelerates Thrombolysis: In Vivo Evaluation of a New Delivery System," Radiology, vol. 168, No. 3, pp. 739-744 (Sep. 1988).

Ritchie et al., "Mechanical Thrombolysis: A New Rotational Catheter Approach for Acute Thrombi," Circulation, vol. 3, No. 5, pp. 1006-1012 (May 1986).

Tachibana, K., "Enhancement of Fibrinolysis with Ultrasound Energy," Journal of Vascular and Interventional Radiology, vol. 3, No. 2, pp. 299-303 (May 1992).

* cited by examiner

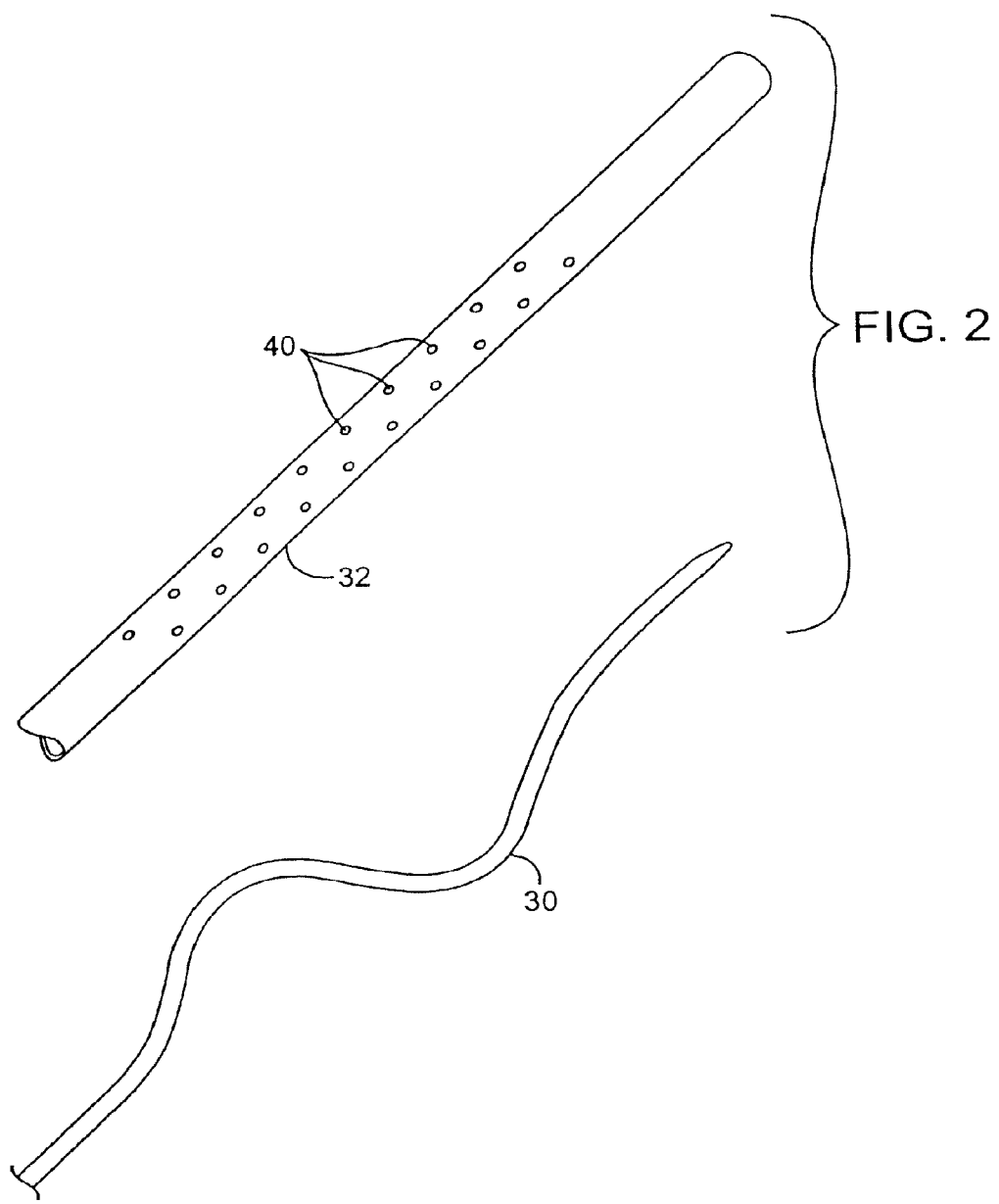

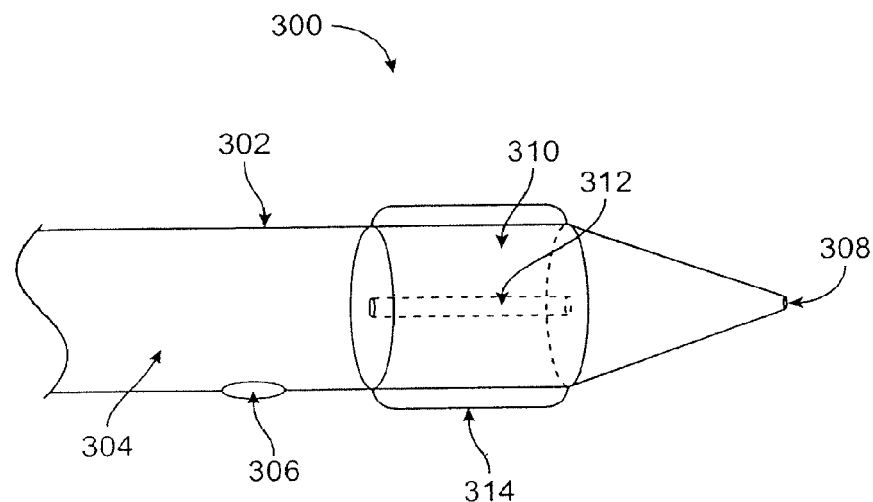
FIG. 16a
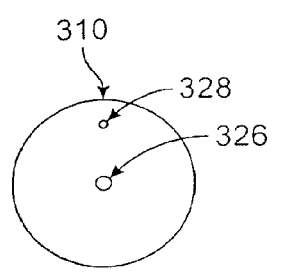 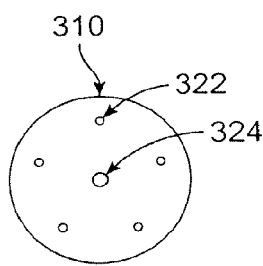 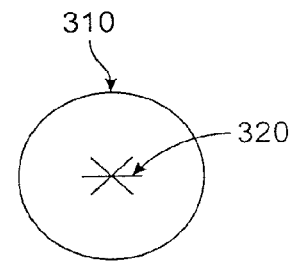
FIG. 16b  FIG. 16c  FIG. 16d

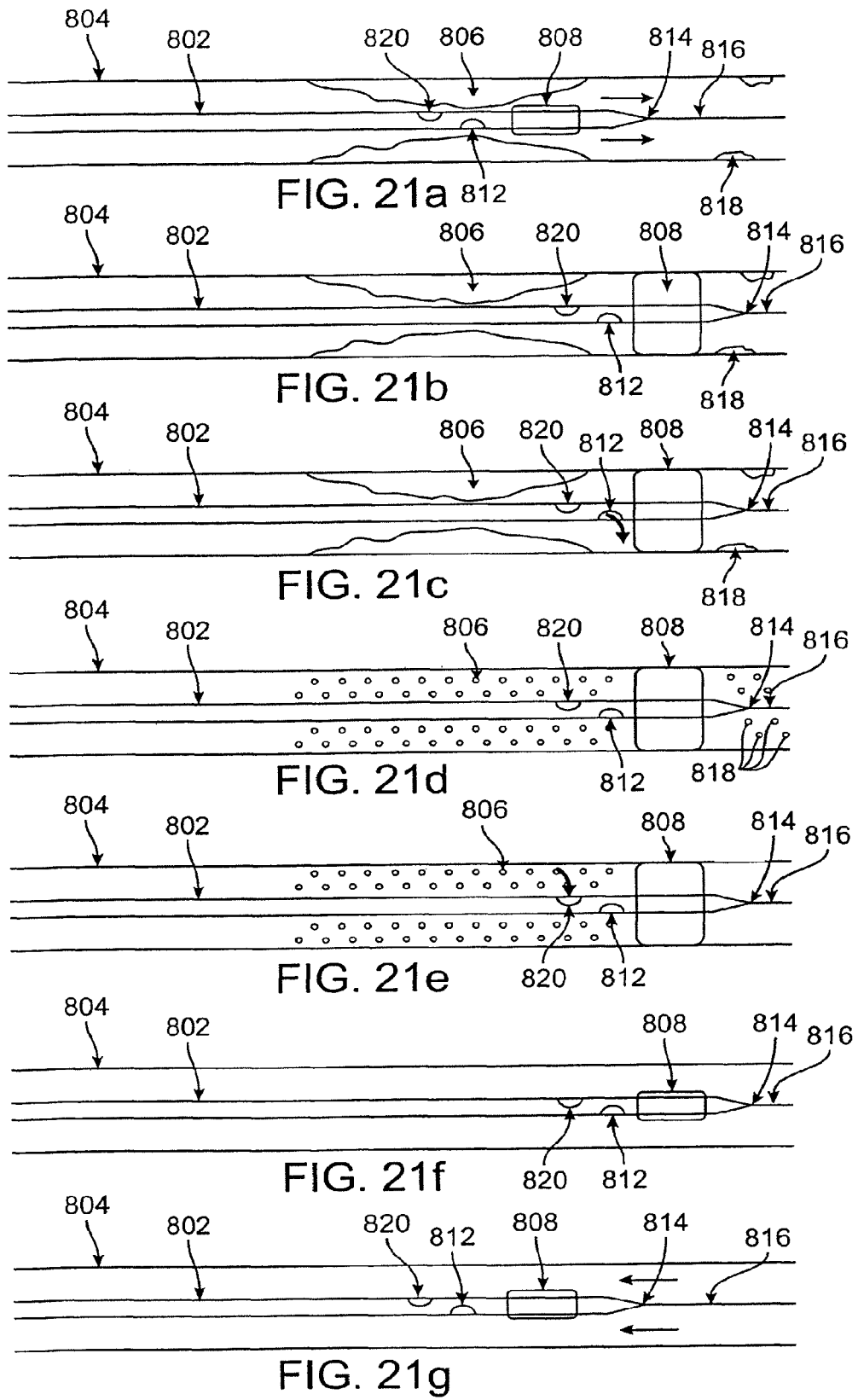

APPARATUS AND METHODS FOR CLOT DISSOLUTION

CROSS-REFERENCES TO RELATED APPLICATIONS

The present application is a divisional of U.S. application Ser. No. 12/816,347, filed on Jun. 15, 2010, now U.S. Pat. No. 8,241,241, which is a continuation of U.S. application Ser. No. 10/142,005, filed on May 8, 2002, now U.S. Pat. No. 7,763,010, which is a continuation-in-part of U.S. application Ser. No. 09/491,401, filed on Jan. 25, 2000, now U.S. Pat. No. 6,663,613, and of PCT/US01/02406, filed on Jan. 24, 2001, the full disclosures of which are incorporated herein by reference.

BACKGROUND OF THE INVENTION

1. Field of the Invention

The present invention relates generally to medical devices and methods. More particularly, the present invention relates to devices and methods for dissolving and disrupting occlusive materials from blood vessels.

Thrombosis and atherosclerosis are common ailments which result from deposition of thrombus or atheromas, respectively, in the luminal walls of blood vessels. When hardened, such deposits typically result in vascular obstruction and reduced blood flow through the lumens of affected blood vessels. Thrombosis and atherosclerosis are most common in the peripheral blood vessels that feed the limbs of the human body and the coronary arteries which feed the heart. Stasis, incompetent valves, and trauma in the venous circulation cause thrombosis, particularly occurring as a deep vein thrombosis in the peripheral vasculature. When such deposits accumulate in localized regions of the blood vessel, they can restrict blood flow and cause a serious health risk.

In addition to forming in the natural vasculature, thrombosis is a serious problem in "artificial" blood vessels or autologous blood vessel grafts, particularly in peripheral femoral-popliteal and coronary bypass grafts and dialysis access grafts and fistulas. The creation of such artificial blood vessels requires anastomotic attachment at at least one, and usually at at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arterio-venous grafts and fistulas which are used for dialysis access are significantly compromised by thrombosis at the sites of anastomotic attachment and elsewhere. Thrombosis often occurs to such an extent that the graft needs to be replaced within a few years or, in the worst cases, a few months.

A variety of methods have been developed for treating thrombosis and atherosclerosis in the coronary and peripheral vasculature as well as in implanted grafts and fistulas. Such techniques include surgical procedures, such as coronary artery bypass grafting, and minimally invasive procedures, such as angioplasty, atherectomy, thrombectomy, thrombolysis, transmyocardial revasculaturization, and the like.

Of particular interest to the present invention, a variety of techniques have been developed for dissolving clot using thrombolytic agents, such as tissue plasminogen activator (tPA), streptokinase, urokinase, and the like. While such thrombolytic agents can be delivered systemically, the present invention is most particularly concerned with the local delivery of such agents and even more particularly concerned with the local delivery of such agents in combination with mechanical clot disruption.

Thrombolytic agents can be very effective at attacking and dissolving relatively soft clot, such as that formed in deep veins. Such agents, however, require time to act, and local delivery catheters often employ isolation balloons to provide high local concentrations of the active thrombolytic agents. Even with such enhanced concentrations, the agents can take extended periods to act, rendering the treatments lengthy and inefficient. In some instances, extensive regions of clot simply cannot be effectively treated using thrombolytic agents alone. In such cases, it has been further proposed to provide a mechanical element to disrupt the clot while the thrombolytic agents are being delivered. See, for example, U.S. Pat. No. 5,947,985 to Mir A. Imran. This patent describes a catheter having axially spaced-apart balloons for isolating a treatment region within a blood vessel. The catheter includes a port for delivering thrombolytic agent between the spaced-apart balloons and a helical wire for removing clot material from the wall to assist in aspiration. While a promising technique, this catheter is not optimized to enhance delivery and mixing of the thrombolytic agent directly into the clot being treated.

For these reasons, it would be desirable to provide improved apparatus, methods, and kits for disrupting and dissolving vascular thrombosis, particularly soft clot of the type found in deep vein thrombosis. It would be particularly desirable to provide methods and apparatus which can enhance the thrombolytic activity of thrombolytic agents delivered to the region being treated, and even more particularly enhance the direct introduction into and mixing of the thrombolytic agent within the mass of clot within the blood vessel. It would also be desirable to provide methods and apparatus which provide infusion of thrombolytic agents, aspiration of fluid and/or clot, and passing of a guidewire through a common lumen, with a majority of infusion and aspiration occurring through an opening in the lumen adjacent the clot. At least some of these objectives will be met by the inventions described hereinafter.

2. Description of the Background Art

Clot disruption catheters which combine the delivery of thrombolytic agents with mechanical disruption are described in, for example, U.S. Pat. Nos. 5,972,019 and 5,947,985. Other clot disruption catheters are described in, for example, U.S. Pat. Nos. 5,954,737; 5,795,322; 5,766,191; 5,556,408; 5,330,484, 5,279,546; 5,116,352; 5,014,093; and WO 96/01591. Catheters having axially spaced-apart isolation balloons for treating thrombus are shown in, for example, U.S. Pat. Nos. 5,947,985 and 5,279,546 and WO 97/11738. Catheters having helical and non-linear guidewires are described in U.S. Pat. Nos. 5,584,843; 5,360,432; 5,356,418; and 5,312,427. Other patents and patent publications of interest include U.S. Pat. Nos. 6,346,116 B1, 6,312,444 B1, 5,957,901; 5,951,514; 5,928,203; 5,908,395; 5,897,567; 5,843,103; 5,836,868; 5,713,848; 5,643,228; 5,569,275; 5,549,119; 5,540,707; 5,501,694; 5,498,236; 5,490,859; 5,380,273; 5,284,486; 5,176,693; 5,163,905; 4,923,462; 4,646,736; and 4,445,509; and WO 99/23952 and WO 99/04701. Publications of interest in the medical literature include LeVeen et al. (1992), American Heart Association Poster Presentation; Tachibana (1993) *JVJR* S:299-303; Kandarpa et al. (1998) *Radiology* 168: 739-744; Bildsoe et al. (1989) *Radiology* 171: 231-233; and Ritchie et al. (1986) *Circulation* 73: 1006-1012.

BRIEF SUMMARY OF THE INVENTION

The present invention provides apparatus, methods, and kits for disrupting and dissolving thrombus, also referred to as clot, present in a patient's vasculature, including both the arterial and venous vasculature, as well as grafts. The present invention is particularly intended for treating thrombotic disease within the venous vasculature, such as thrombosis in the superficial vein, the central veins, the femoral-popliteal veins, the iliofemoral vein, and the like. The present invention is also particularly intended for treating arterial thrombotic disease, such as thrombosis in the iliofemoral artery, the superficial femoral artery, and the like.

The present invention is advantageous in a number of respects. In particular, the methods and apparatus of the present invention will provide improved introduction and mixing of thrombolytic agents into vascular clot, which in turn will improve the efficiency of clot dissolution, including both reducing the time required for dissolution and/or enhancing the degree to which the clot is dissolved, i.e., reducing the particle size of clot achieved at the end of treatment. The reduction of treatment time will reduce both the cost of treatment and the time during which the patient is undergoing the treatment. The improved degree of clot dissolution will reduce the danger of released emboli, which can be a serious risk to the patient.

Various embodiments of the present invention provide apparatus and methods for infusing thrombolytic agents, aspirating clot and/or fluid, and passing a guidewire through a common catheter lumen. Other embodiments provide for separate lumens for infusing, aspirating and/or passing a guidewire. Generally, the embodiments described provide advantageous alternatives for accomplishing desired infusion, aspiration and/or positioning tasks during a clot disruption procedure. Embodiments with only one or two lumens may provide the additional advantage of having a relatively smaller diameter than other devices.

In a first aspect, apparatus for disrupting clot over a luminal length of a blood vessel according to the present invention comprises a catheter body having a proximal end, a distal end and at least one lumen. The lumen includes a distal-end opening for allowing passage of a guidewire and fluid flow and at least one side opening proximal to the distal-end opening for allowing fluid flow. The distal-end opening and the at least one side opening generally allow preferential fluid flow through the at least one side opening. The catheter body further includes a first radially expandable body between the distal-end opening and the side opening in the lumen, for inhibiting flow of clot beyond the luminal length of the blood vessel.

The dimensions and materials of the catheter body will be selected according to the target site within the vasculature to be treated, i.e., the catheter will be sized to be introduced percutaneously or via a cut down to the vasculature at an entry and then be intravascularly advanced, typically over a guidewire, to the target site. Target sites in the peripheral, coronary, and cerebral vasculature will generally be approached through different access sites and will require catheters having different lengths, diameters, and flexibilities. The constructions of such catheters, however, are well-known and well-described in the patent and medical literature.

The luminal length of the blood vessel will usually be at least 3 cm, more usually being at least 10 cm, and typically being in the range from 3 cm to 100 cm, usually from 5 cm to 40 cm. The length of thrombotic disease being treated will vary depending on the location of the disease within the vasculature. For example, deep vein thrombosis will often be disseminated over a length in the range from 5 cm to 100 cm. The apparatus and methods of the present invention will be capable of treating disease disseminated over these lengths as described in more detail below. The apparatus of the present invention need not be adapted to treat the entire length of the diseased region at once. It will often be possible and in some cases desirable to treat discrete lengths within the entire diseased region separately. Such discrete lengths can be treated successively, e.g., by axially translating the treatment device within the blood vessel being treated. Alternatively, the segments could be treated using different devices, optionally introduced from different introduction sites in the vasculature.

In some embodiments of the invention, infusion of an agent, aspiration of clot and fluid, and/or passage of a guidewire may be performed through a common lumen. In other embodiments, two or more lumens are used for infusion, aspiration, and guidewire passage. For example, in one embodiment infusion and guidewire passage may occur through one lumen and aspiration may occur through another. In other embodiments, aspiration and guidewire passage may occur through the same lumen and infusion may occur through another. Thus, some embodiments of the present invention provide for infusion and aspiration through the distal-end opening and the at least one side opening, while other embodiments divide these tasks among multiple lumens. Furthermore, many embodiments of the invention allow for a guidewire to remain in place within the at least one lumen while either infusion, aspiration, or both are performed through the distal-end opening and the at least one side opening.

As described briefly above, the distal-end opening and the at least one side opening are generally configured to allow for preferential fluid flow through the at least one side opening. This preferential flow may be accomplished in any of a number of suitable ways. For example, distal-end opening may be configured to have a cross-sectional area that is significantly smaller that the cross-sectional area of the at least one side opening. In one embodiment, the distal-end opening may have a cross-sectional area of between about 0.1% and about 20%, and preferably between about 1% and about 5%, of the cross-sectional area of the at least one side opening. This difference in cross-sectional areas of the openings will allow a preferential fluid flow through the at least one side opening because fluid will preferentially flow through the larger opening, with the least resistance.

In various embodiments, the at least one side opening may include one opening in a side wall of the lumen of the catheter body, multiple smaller spaced-apart openings in the lumen, a combination of multiple smaller openings and one larger opening, and the like. Generally, the at least one side opening may have any suitable configuration for infusing an agent and/or aspiration clot and fluid.

In other embodiments, the apparatus allows for preferential fluid flow through the at least one side opening by further including a flow resistor between the distal-end opening and the at least one side opening for inhibiting fluid flow through the at least one lumen. Generally, the flow resistor may comprise any mechanism for inhibiting fluid flow through the at least one lumen such that fluid flow in aspiration and/or infusion occurs preferentially through the at least one side opening. For example, in one embodiment, the flow resistor allows fluid flow (either infusion, aspiration or both) through the distal-end opening at a rate of between about 0.1% and about 20% of the total fluid flow, and preferably between about 1% and about 5% of the total flow. Thus, fluid flow through the at least one side opening would account for between about 80% and about 99.9% of the fluid flow, and preferably between about 95% and about 99% of the total flow.

Generally, the optional flow resistor disposed between the distal-end opening and the at least one side opening may have any of a number of suitable configurations for inhibiting flow through the at least one lumen to allow preferential flow through the at least one side opening. In one embodiment, the flow resistor comprises a cylindrical material with at least one channel. Such a flow resistor may be made from any suitable material, such as a silicone-based material. Typically, the cylindrical material will have an outer diameter equal to the inner diameter of the at least one lumen. The at least one channel through the cylindrical material may have any of a number of different configurations in various embodiments of the invention. For example, in one embodiment the channel comprises a cylindrical hole having an inner diameter sufficient to allow passage of a guidewire. The same hole may also allow passage of fluid. In another embodiment, the at least one channel comprises one or more flexible slits to allow passage of the guidewire and fluid. In yet another embodiment, the at least one channel comprises a valve for allowing passage of the guidewire and one or more holes for allowing passage of fluid. Generally, any suitable configuration for the cylindrical material and the at least one channel may be used to inhibit flow of fluid through the lumen distal to the flow resistor.

In another embodiment, the flow resistor comprises a membrane with at least one aperture. In yet another embodiment, the flow resistor comprises a ball valve for partially blocking flow of fluid through the at least one lumen, the ball valve having at least one channel, a ball, and a widened area within the channel into which the ball may fall to allow passage of a guidewire through the channel. In yet another embodiment, the flow resistor comprises a compliant membrane coupled to the at least one lumen, the compliant membrane communicating with an inflation lumen, the inflation lumen communicating with an inflation port. Inflation via the inflation port and inflation lumen moves the compliant membrane to partially or wholly block fluid flow through the at least one lumen of the catheter body. Such an inflation lumen may be separate from or in communication with an inflation lumen for an expandable body on the catheter body.

Whether a particular embodiment of the present invention uses different cross-sectional areas of the distal-end opening and the at least one side opening, an optional flow resistor, a combination thereof, or some other suitable means, invariably a preferential fluid flow is allowed through the at least one side opening. Such a preferential flow generally allows aspiration and/or infusion to be concentrated at a clot site or treatment site adjacent the at least one side opening. At the same time, some aspiration and/or infusion still typically occurs through the distal-end opening, which may be advantageous in various procedures, for example where some infusion of a thrombolytic agent at a location distal to the clot is desired.

Some embodiments of the present invention further include a mechanical agitator near the distal end of the catheter body for mechanically agitating clot over the length of the blood vessel. The mechanical agitator may have a wide variety of specific configurations. Usually, the mechanical agitator will comprise a radially expansible agitator which is rotatable and/or axially translatable relative to the catheter body. In one embodiment, the radially expansible agitator will be self-expanding, e.g., it may comprise a resilient element which may be radially constrained to have a low profile (small diameter) and may be freed from radial constraint to have an enlarged profile (large diameter) with a non-linear geometry. Typically, radial constraint can be provided by a sleeve or sheath which may be axially advanced and retracted relative to the catheter body to cover and uncover the radially expansible agitator. In this way, the catheter can be introduced to a target site within the vasculature with the expansible agitator covered (and thus radially constrained). After the desired target site is reached, the sheath or sleeve can be axially retracted to release the radially expansible agitator so that it expands to engage the clot in the blood vessel. The agitator may then be rotated and/or axially translated to engage and disrupt the clot in combination with the release of a thrombolytic agent, as described in more detail below. Such rotation, oscillation, and/or translation will usually be accomplished using a motor drive unit operatively connected to the agitator, but could in some instances be performed manually in whole or in part.

In an alternative embodiment, the radially expansible agitator may comprise a resilient element which can be axially shortened to assume an enlarged profile having a nonlinear geometry. For example, a self-expanding resilient element may be straightened (tensioned) by initially positioning a rod or stylet therein in order to lengthen the element and cause it to straighten to a low profile diameter. The agitator may then be expanded by retracting the rod or stylet to release the agitator from tension and permit the agitator to radially expand as a result of the agitator's inherent spring force. Alternatively, the agitator may be knitted to have a generally straight, low profile configuration and be actively caused to radially expand by pulling on a rod or wire to cause axial shortening.

In all cases, the agitator may have a variety of specific geometries, such as a helical geometry, a spiral geometry, a serpentine geometry, a zig-zag geometry, an alternating helix geometry (i.e., two or more helical geometries in tandem where successive helixes are wound in opposite directions), and/or a variety of other random geometries. The geometries will be such that the resilient element can engage against and penetrate into the clot within a blood vessel as the resilient element is radially expanded. As the resilient element is thereafter rotated and/or axially translated, the element will then mechanically engage and disrupt the clot. By simultaneously introducing the thrombolytic agent directly to the region which is being mechanically engaged by the agitator, disruption and dissolution of the clot is significantly enhanced.

In other embodiments of the invention, an agent such as a thrombolytic agent may be distributed at the luminal length of the blood vessel by an agent distributing means. In some embodiments, such distributing means will comprise a porous sheath or other perforate or foramenous structure which may be disposed over a radially expansible agitator. The porous sheath may be a thin fabric having a generally uniform porosity along its length. Alternatively, the sheath could be an impermeable membrane having a plurality of holes or ports formed along its length to permit the release of a thrombolytic agent. A wide variety of other perforate or porous structures will also be available. For example, the sheath could comprise a coil having a plurality of successive turns, where bending of the coil causes the turns to separate, creating spaces or apertures for the release of the thrombolytic agent. It would also be possible to form the sheath from an elastic material having pores which are generally closed but which open when the elastic material is tensioned, either by stretching (e.g., due to internal pressurization with the thrombolytic agent) or by deforming the elastic sheath material as the sheath is deformed into its non-linear geometry.

In embodiments of the invention which include a mechanical agitator, the sheath may be able to release the thrombolytic agent along substantially the entire length of the agitator which is in contact with the clot to be disrupted. In this way, the thrombolytic agent will be released at the point of mechanical agitation, resulting in both improved distribution of the thrombolytic agent into the clot as well as improved disruption and dissolution of the clot. Usually, the porous sheath will be formed as a relatively closely fitting sleeve over the resilient element, e.g., so that the sheath assumes the same non-linear geometry as the resilient element. Alternatively, however, the sheath may be formed to have larger diameter, e.g., a diameter approaching the luminal diameter of the blood vessel being treated. In the latter case, the thrombolytic agent may be distributed over the entire region of the clot while the agitator presses the sheath into the clot to enhance introduction of the thrombolytic agent and dissolution of the clot. In both cases, the sheath may be elastic, i.e., expansible in response to pressure of thrombolytic agent, or inelastic. Alternatively, the sheath could be a composite of an elastic fabric or membrane reinforced with a grid or network of elastic or inelastic ribs or other reinforcement members.

In an alternative embodiment, the agitator may be configured to directly deliver the thrombolytic agent into the clot as the agitator is being driven. For example, when the agitator is in the form of a non-linear element, the element may be formed as a tube having a thrombolytic agent delivery lumen therein. The tube may then be provided with agent delivery ports and/or porous regions to permit the generally uniform release of the thrombolytic agent over the length of the element which is contact with the clot. In this way, the thrombolytic agent may be delivered directly into the clot and dissolution enhanced without the need to provide for a separate thrombolytic agent delivery sheath.

Optionally, the clot disruption and dissolution apparatus of the present invention may further comprise means for isolating at least a distal end of the catheter body to reduce blood flow through the region being treated by the catheter. For example, at least a single balloon may be provided on the catheter body distally or proximally of the agitator and thrombolytic agent distribution means on the catheter. When only a single balloon is used for isolation, it will preferably be on the side of the thrombolytic agent distribution means which is downstream from the region being treated. In this way, the isolation balloon will inhibit the loss of the thrombolytic agent as well as the release of emboli downstream. Preferably, isolation means will be provided both on the distal end proximal sides of the agitator and thrombolytic agent distributing means. Typically, the isolation means will comprise a pair of axially spaced-apart balloons disposed on the catheter body. Further optionally, one of the balloons may be disposed on a separate, telescoping portion of the catheter body in order to permit length adjustment of the region to be isolated. Alternatively, a variety of other isolation means, such as deployable flanges, malecot structures, expansible braids, and the like, could also be employed.

In the apparatus of the present invention which employ both an agitator and a sheath, the agitator may optionally be replaceable within the sheath and/or axially translatable within the sheath. Still further optionally, the sheath itself may be introduceable over a guidewire, either with or without the agitator being in place within the sheath. Thus, the apparatus may provide for the free interchangeability of two or more agitators and at least one guidewire for initially placing the sheath. It will be appreciated that such replaceability provides great adaptability of the systems of the present invention. For example, the sheath could be introduced to a treatment site within the vasculature over a conventional guidewire or a guidewire with a balloon and/or filter on it. After withdrawing the guidewire, a first agitator could be introduced to within the sheath and the target site treated by both agitation and release of the thrombolytic agent. It would then be possible to reposition the agitator within the sheath to treat a different region of the vasculature. Alternatively or additionally, it would be possible to remove the first agitator and replace it with a second agitator selected to better treat the region and/or to provide for a subsequent treatment step of that region.

The catheters of the present invention may optionally be provided with lumen(s) for introduction over a guidewire or a guidewire with a balloon and/or filter on it. For example, the catheter (or a sheath component thereof) may be introduced over a guidewire using a central lumen which also receives the agitator. Alternatively, separate guidewire lumen(s) could be provided on the sheath or elsewhere, e.g., a short guidewire lumen could be provided near the distal tip of the sheath beyond the non-linear region defined by the agitator. Such a short lumen would avoid interference with the agitator. Inflation of a guidewire balloon distal of the catheter may help isolate the region of the vessel from blood flow. A variety of specific designs will be available.

The apparatus of the present invention will still further be available of systems comprising at least one sheath together with two or more agitators which are removably replaceable within the sheath. Such systems allow for treatment of different diseases and different regions of the vasculature. The treating physician can either choose the initial combination which is best for a particular disease, or may begin treatment with one combination of sheath and agitator and continue treatment thereafter with another combination of sheath and agitator.

In another apparatus aspect, the invention provides an apparatus for disrupting clot over a target region of a blood vessel. The apparatus comprises a catheter body having a proximal end and a distal end. An agitator is disposed near the distal end for mechanically agitating clot over the target region. A port near the distal end is in fluid communication with an agent supply source for distributing an agent along the target region.

In many embodiments, the agent will comprise a thrombolytic agent, which may provide an enzymatic action to break down fibrin clot matrix. A variety of other agents may also be used, including group IIb/IIIa Inhibitors (typically to inhibit fibrinogen binding site of platelet membrane, other anti-platelet agents, anti-thrombin agents and agents directed toward prevention of restenosis (which may inhibit coagulation and/or inhibit restenosis by decreasing smooth muscle proliferation and migration), gene therapeutic agents (currently under development, often for preventing restenosis and promoting angiogenesis), chemotherapeutic agents (generally designed to treat malignancies) imaging media, and/or other potential agents.

The present invention still further provides a method for disrupting clot over a luminal length of a blood vessel. The method includes first positioning a catheter body with at least one lumen at a location within the luminal length of the blood vessel. The at least one lumen of the catheter body has a distal-end opening and at least one side opening. The method then includes infusing an agent through the distal-end opening and the at least one side opening, where the infusion predominantly occurs through the at least one side opening.

Optionally, methods of the present invention also include mechanically agitating the clot over the luminal length of the blood vessel. In some embodiments, the methods comprise infusing the thrombolytic agent in a distributed pattern over the treated length. By "distributed pattern," it is meant that the thrombolytic agent is not simply released into the treatment region but rather that it is introduced directly into the clot at the interface region where the clot is being mechanically agitated. For example, in the case where mechanical agitation is achieved using a non-linear element, the thrombolytic agent will be delivered at points which are distributed over the non-linear element so that they enter the clot at the "point of attack" described above in connection with the apparatus. The thrombolytic agent can be delivered using a porous sheath which is disposed over the non-linear agent in a sleeve-like manner. Alternatively, the thrombolytic agent can be delivered through a lumen within the non-linear agent and released through a plurality of ports or porous regions in the non-linear element. In both cases, the ability to deliver the thrombolytic agent directly into the clot as it is being mechanically penetrated by the element will enhance distribution of the thrombolytic agent within the clot and improve the efficiency of clot dissolution as well as decrease the particle size reduction achieved in a given period of time.

In specific aspects, the methods of the present invention are used to treat predetermined luminal lengths, typically having a length of at least 5 cm, usually at least 100 cm, and most usually in the range from 10 cm to 50 cm. When the blood vessel is a vein, the targeted regions may be selected from the group consisting of vena cava, iliac vein, femoral vein, popliteal vein, common iliac vein, external iliac vein, brachial vein, and subclavian vein. When the target blood vessel is an artery, the preferred arteries are the internal iliac artery, external iliac artery, popliteal artery, coronary arteries, superficial femoral artery, and the brachial artery.

Preferably, mechanical agitation comprises rotating and/or axially translating a radially expansible agitator within the blood vessel and against the clot. The exemplary agitators have been described above. Optionally, the mechanical and agitation and thrombolytic agent delivery may be performed within isolated regions of the vasculature, typically provided by inflating one or more balloons within the vasculature at either side of the treatment region. Most preferably, a pair of axially spaced-apart balloons will be disposed on either side of the treatment region to provide isolation, both to maintain higher thrombolytic agent concentrations within the region and to inhibit the release of thrombotic clot prior to sufficient dissolution of the clot.

The methods of the present invention allow for a wide variety of particular treatment protocols. For example, the agitator may be driven at different and/or variable speeds. Typically, the agitators will be rotated and/or oscillated at speeds in the range from 0 rpm to 50,000 rpm, preferably from 50 rpm to 5,000 rpm. The speeds may be set and/or adjusted at a wide variety of particular rotational speeds within these ranges. In some cases, the direction of the rotation can be reversed during the course of the procedure. It will further be possible to axially advance or retract the agitator, optionally within a sheath, during the course of treatment to enhance the disruption of the clot and introduction of the thrombolytic into the clot. Still further additionally, it will be possible to vary the width or diameter of the agitator during the course of treatment to enhance disruption.

In general, infusing the agent predominantly through the at least one side opening is accomplished via a larger cross-sectional area of the side opening compared to the distal-end opening, via a flow resistor, or by any other suitable means, as described in greater detail above in relation to apparatus of the invention. In some embodiments, one or more agents may be infused through the lumen of the catheter body and clot and/or fluid may be aspirated through the same lumen. In other methods, infusion and aspiration may be performed through separate lumens. In still other embodiments, infusion is performed through a sheath surrounding the catheter body and aspiration is performed through the lumen of the catheter body. In other methods, infusion is through the lumen and aspiration is through the sheath. In some of the embodiments, a guidewire may be left in position in one lumen during infusion, aspiration or both.

As just suggested, the treatment methods of the present invention may optionally comprise aspiration of the disrupted clot from the treatment site. Aspiration may be accomplished using a lumen or lumens within the sheath and/or agitator to withdraw the disrupted clot. Optionally, mechanical means, such as an Archimedes screw or other pump, may be incorporated into the catheter to enhance the aspiration and removal of the disrupted clot. In other embodiments, such a pump may be mounted to a separate structure, such as to a sheath removably disposed over the catheter, an inner structure removably disposed within a lumen of the catheter, or the like. Still further embodiments may rely on an aspiration means which remains outside the patient, such as a syringe, vacuum container, or the like.

Still further optionally, the disrupted clot and other fluid or fluidized materials within the treatment region may be recirculated to enhance breakup of the clot and activity of thrombolytic agent. For example, pairs of spaced-apart ports or apertures on the sheath may be used to draw in the material within the treatment region and expel that material at a different point within the treatment region. Such recirculation may significantly enhance the thrombolytic activity and decrease the treatment time.

As a still further option, it is possible to periodically or continuously introduce blood into the treatment region. tPA acts on plasminogen within the vasculature to breakup thrombus. If the treatment region of the present invention is isolated, it may be beneficial to introduce fresh blood containing plasma in order to enhance the activity of the thrombolytic agent, particularly tPA. Most simply, fresh blood could be introduced by periodically opening an isolation balloon which isolates the treatment region.

The methods of the present invention can rely on two or more of the treatment catheters to be used simultaneously. For example, in the treatment of arterio-venous grafts, it is possible to introduce two treatment catheters according to the present invention, each of which has a balloon or other occlusion device at its distal end, to an A-V graft at a point near its middle. By introducing the two treatment catheters in opposite directions, the graft can be isolated very close to the points at which it is anastomosed to the natural vasculature. After such isolation is achieved, the interior of the A-V graft can then be cleaned out according to the methods of the present invention, and preferably the released clot and thrombus may be withdrawn through an access sheath to the A-V graft.

The present invention still further comprises kits, including a catheter having an agitator in a thrombolytic agent delivery means. The kits will further include instructions for use according to any of the methods set forth above. In addition to the catheter and the instructions for use, the kits will usually further comprise packaging, such a box, pouch, tray, tube, bag, or the like, which holds the catheter and the instructions for use. Usually the catheter will be maintained sterilely within the package, and the instructions for use will be printed on a separate package insert or piece of paper. Alternatively, the instructions for use may be printed in whole or in part on a portion of the packaging.

BRIEF DESCRIPTION OF THE DRAWINGS

FIG. 2 is a detailed view of the distal end of the clot disruption apparatus of FIG. 1, showing the sheath and agitator components thereof.

FIG. 16a illustrates a cross section of the distal end of a clot disruption apparatus having a cylindrical flow resistor and a common lumen for infusion and aspiration, according to one embodiment of the present invention.

FIGS. 16b-d illustrate frontal views of various configurations of a flow resistor for a clot disruption apparatus as in FIG. 16a.

FIGS. 21a-g illustrate a method for disrupting a clot according to another embodiment of the present invention.

DETAILED DESCRIPTION OF THE INVENTION

Figure 1:
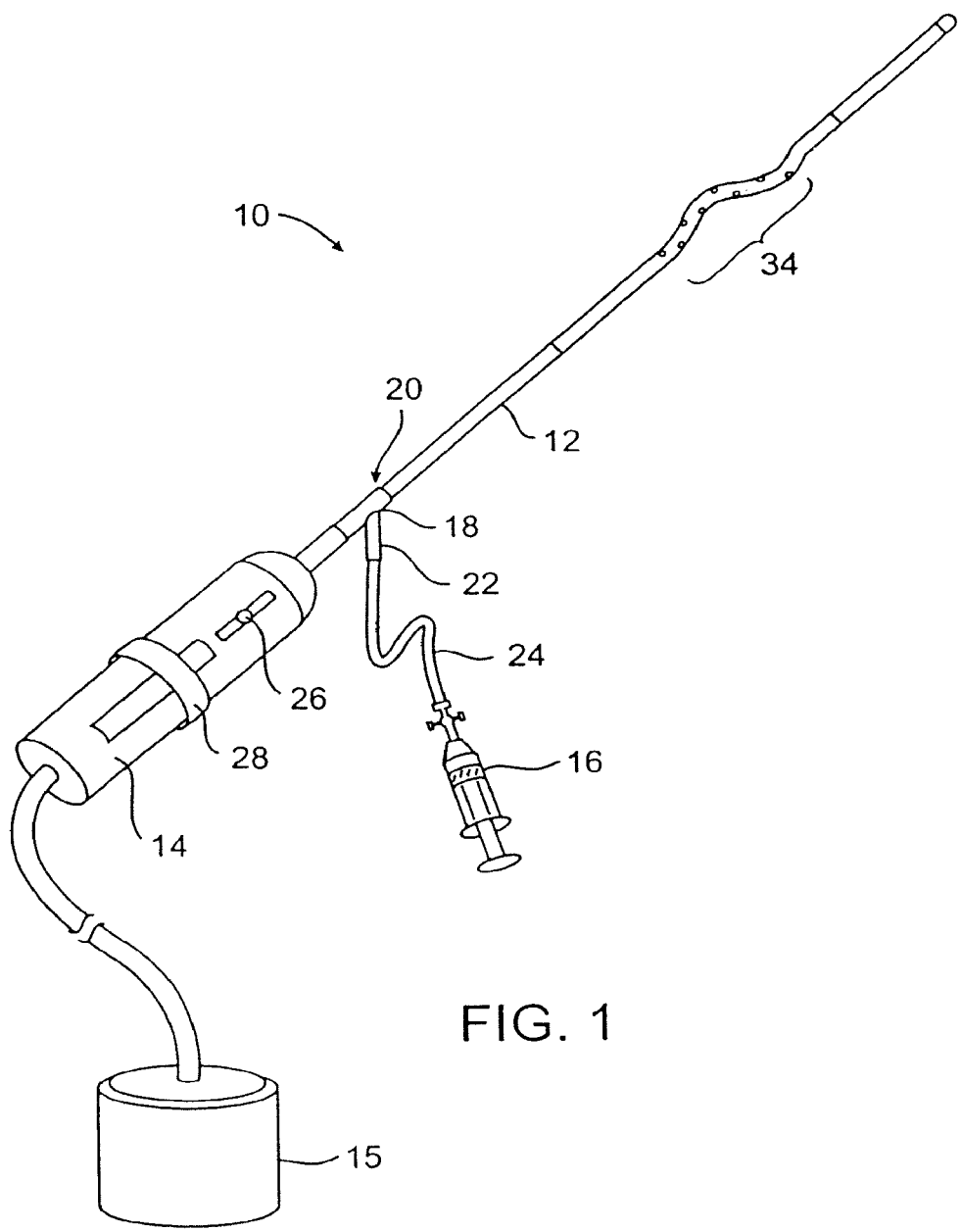
FIG. 1 is a perspective view of clot disruption apparatus constructed in accordance with the principles of the present invention.

In FIG. 1, a clot disruption apparatus 10 is shown to comprise a catheter body 12, a motor drive unit 14, and a thrombolytic agent delivery device 16. The motor drive unit 14 is attached to a hub 18 at a proximal end 20 of the catheter body 12. The thrombolytic agent delivery device is shown as a syringe which is attached to a side port 22 on hub 18 through a conventional tube 24. It will be appreciated that other thrombolytic agent delivery devices could also be used, such as pumps, gravity bags, and the like. The thrombolytic agent delivered by device 16 can be any conventional bioactive agent which is capable of disrupting and dissolving clot and thrombus, such as tissue plasminogen activator (tPA), streptokinase, urokinase, heparin, low molecular weight heparin, and the like. The thrombolytic agents may be delivered through the delivery device 16 as a bolus, continuously over time, or as combinations thereof.

Use of the present invention will generally be described with reference to thrombolytic agents, often those having enzymatic action which breaks down fibrin clot matrix. In addition to tPA, suitable thrombolytic agents may include Alteplase or Activase™, Tenecteplase, TNK, and TNKase™, all of which are from Genentech, Inc; Anistreplase, a-SK, Eminase™, from Roberts Pharmaceuticals; Reteplase, r-PA, Retavase™, from Centocor, Inc.; Streptokinase, SK, Streptase™, from AstraZeneca, Inc.; and Abbokinase™, Abbott, Inc. A variety of other agents may also be used, including Group IIb/IIIc Inhibitors which may inhibit fibrinogen binding site of platelet membrane, such as Abciximab and ReoPro™, from Centecor, Inc.; Tirofiban and Aggrastat™ from Merck, Inc.; Eptifibatide and Integrelin™ from Cor Therapeutics, Inc.; and other IIb/IIIa inhibitors such as Bitistatin and Kistrin, or other anit-platelet agents (such as aspirin).

The invention may also be used with anti-thrombin agents and agents directed toward prevention of restenosis to inhibit coagulation and/or inhibit restenosis by decreasing smooth muscle proliferation and migration, such as Heparin (LMW containing most anticoagulant activity, and also inhibits smooth muscle proliferation and migration), enoxaparine or Lovenox™, dalteparin or Fragmin™, and ardeparin or Noimoflo™, Hirudin, Argatroban, PPACK to inhibit thrombin induced platelet activation and platelet secretion of PDGF which may be responsible for smooth muscle proliferation and migration, radioactive agents (such as for vascular brachytherapy, inhibits smooth muscle proliferation), locally delivered nitrate (nitric oxide, prevents reflex vasoconstriction at site of injury and inhibits activation of circulating platelets in order to decrease late luminal narrowing), HA 1077 (which inhibits action of cellular protein kinases and sequestration of cellular calcium, acts as vasodilator, and may inhibit smooth muscle proliferation), and other anti-restenosis agents (such as calcium antagonists, angiotensin converting enzyme inhibitor, anti-inflammatory agents, steroidal agents, anti-mitotic agents, HMG CoA reductase inhibitors, colchicine, angiopeptin, cytoclasin B (inhibits actin polymerization and muscle cell motility.

In still further alternatives, the invention may be used with gene therapeutic agents, new agents and/or agents which under development for preventing restenosis and promoting angiogenesis. Such agents may be delivered via plasmid vectors or by viral vectors. Examples include genes relating to: VEGF, C-myb, FGF, transforming growth factor b, endothelial growth factor, protooncogenes such as C-myc, C-myg, CDC-2, and PCNA.

Still further alternative agents may be used with the devices and methods of the present invention, including chemotherapeutic agents (agents used to treat malignancies, such as adriamycin or Doxorubicin™), imaging media (including contrast media and radioactively labeled agents), plasminogen additive (as an adjunct to thrombolytic therapy), immunosuppressive agents, and other potential agents.

A motor drive unit 14 includes a sliding switch 26 which controls the rotational speed of the motor and a sliding collar 28 which controls the axial position of an agitator 30 within a sheath 32 of the catheter body 12 (FIG. 2). A non-linear region 34 of the catheter body 12 is defined by the agitator 30 within the sheath 32. By axially translating the agitator 30 using the collar 28, the non-linear region of the catheter body can be moved in a proximal or distal direction along the catheter body. The motor drive unit will be capable of rotating the agitator 30 within the sheath 32 at the rotational rates set forth hereinabove. Additionally, the motor drive unit 14 may be adapted in other circumstances to oscillate the agitator, axially reciprocate the agitator, or provide for other mechanical movements of the agitator which can cause or contribute to clot disruption according to the methods of the present invention.

Referring now in particular to FIG. 2, the sheath 32 comprises a tubular body formed from a polymeric material, a fabric, or other material, and includes a plurality of fluid distribution ports 40 along its length. As illustrated, the fluid distribution ports 40 are only formed over a portion of the length of the sheath. It will also be possible to form the ports over the length which is greater than the non-linear region defined by the agitator 30. The agitator 30 is shown to be a short helical section having one complete turn. Other geometries will include two-dimensional geometries, such as single humps, S-shapes, zig-zag patterns, and the like. Suitable three-dimensional geometries include helical geometries, alternating helixes, spirals, and the like. In all cases, as the non-linear region of the agitator is rotated within the sheath, the sheath will be caused to trace a three-dimensional envelope within the blood vessel being treated. Usually, the agitator 30 will force the sheath into engagement with clot or thrombus within the blood vessel, and the thrombolytic agent will be released through the ports 40 as the sheath is being engaged by the agitator. In this way, the thrombolytic agent is introduced directly into the clot or thrombus as the clot is being mechanically disrupted. This combination of mechanical and chemical dissolution of the clot is every effective and can reduce the clot disruption time significantly when compared to other thrombolytic techniques.

As will be described in more detail below, the apparatus of FIGS. 1 and 2 may be used with a variety of additional structures to help remove the disrupted clot material. Optionally, a simple external vacuum source 15 may be coupled to the motor drive unit 14 to draw material proximally through an aspiration lumen of the catheter body. A wide variety of aspiration sources may be used, including a simple locking syringe.

Figure 2A:
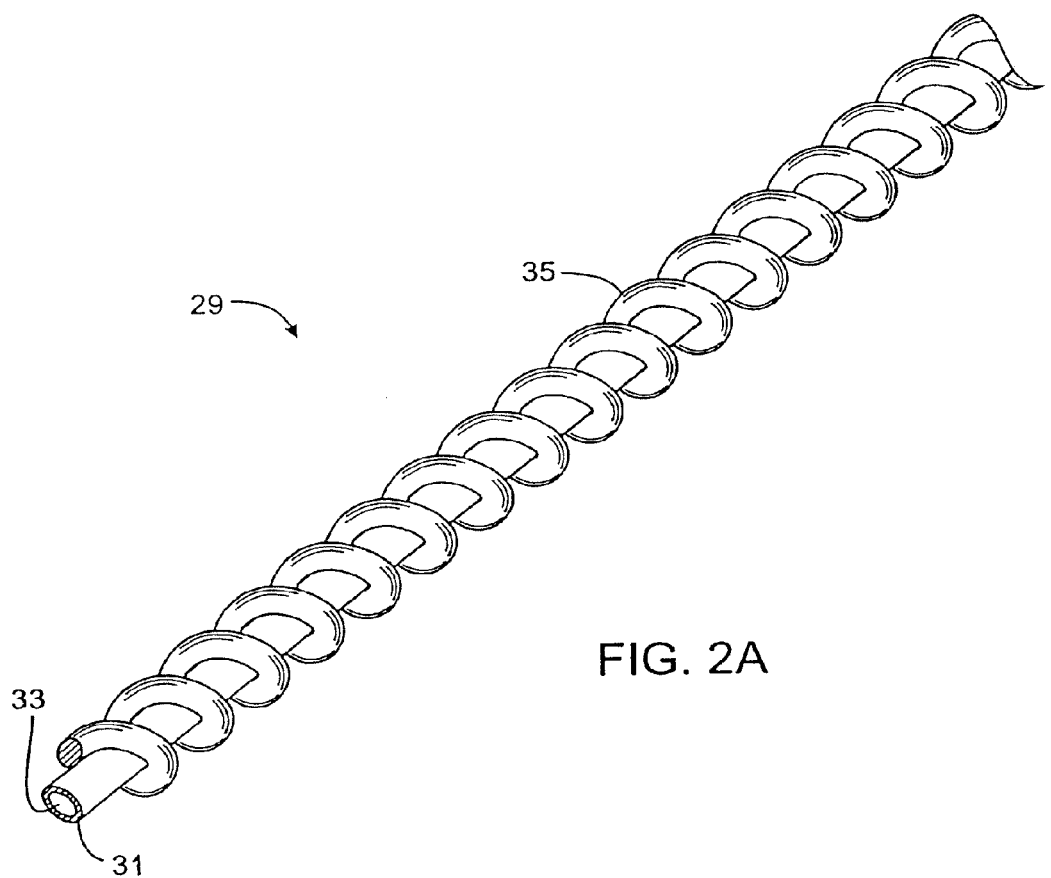
FIG. 2A illustrates an aspiration pump which may be integrated into the apparatus of FIG. 1 for aspiration of disrupted clot material.

In some embodiments, a pump element 29 shown in FIG. 2A may be disposed within the aspiration lumen to help pump the clot material proximally through the catheter body. As described in detail in co-pending application Ser. No. 09/454,517, filed on Dec. 6, 1999, the full disclosure of which is incorporated herein by reference, pump element 29 may comprise a tubular body 31 having a lumen 33 therein and a helical element 35 disposed thereover. When pump element 29 rotates within an aspiration lumen in catheter body 12 (or alternatively, in a sheath surrounding the catheter body or a separate aspiration catheter extending along catheter body 12), material can be urged axially (either proximally or distally, depending on the direction of rotation). Such pumps are sometimes referred to as an "Archimede's screw." Pump element 29 may be formed from at least a portion of a shaft drivingly coupling agitator 30 to the motor drive unit, or may comprise a separately driven structure.

In some embodiments, such as when the region of the blood vessel to be treated will be isolated both proximally and distally, it may be advantageous to maintain a substantially constant fluid volume within the region of the blood vessel. As described in detail in application Ser. No. 09/751,216, filed on Dec. 29, 2000, the full disclosure of which is incorporated herein by reference, an at least roughly equal quantity of fluid (including the therapeutic agent) may be introduced into the vessel as the total volume aspirated from the vessel by filtering the aspirated fluid from the solid clot material and by reintroducing the filtered fluid back into the vessel.

Figure 3:
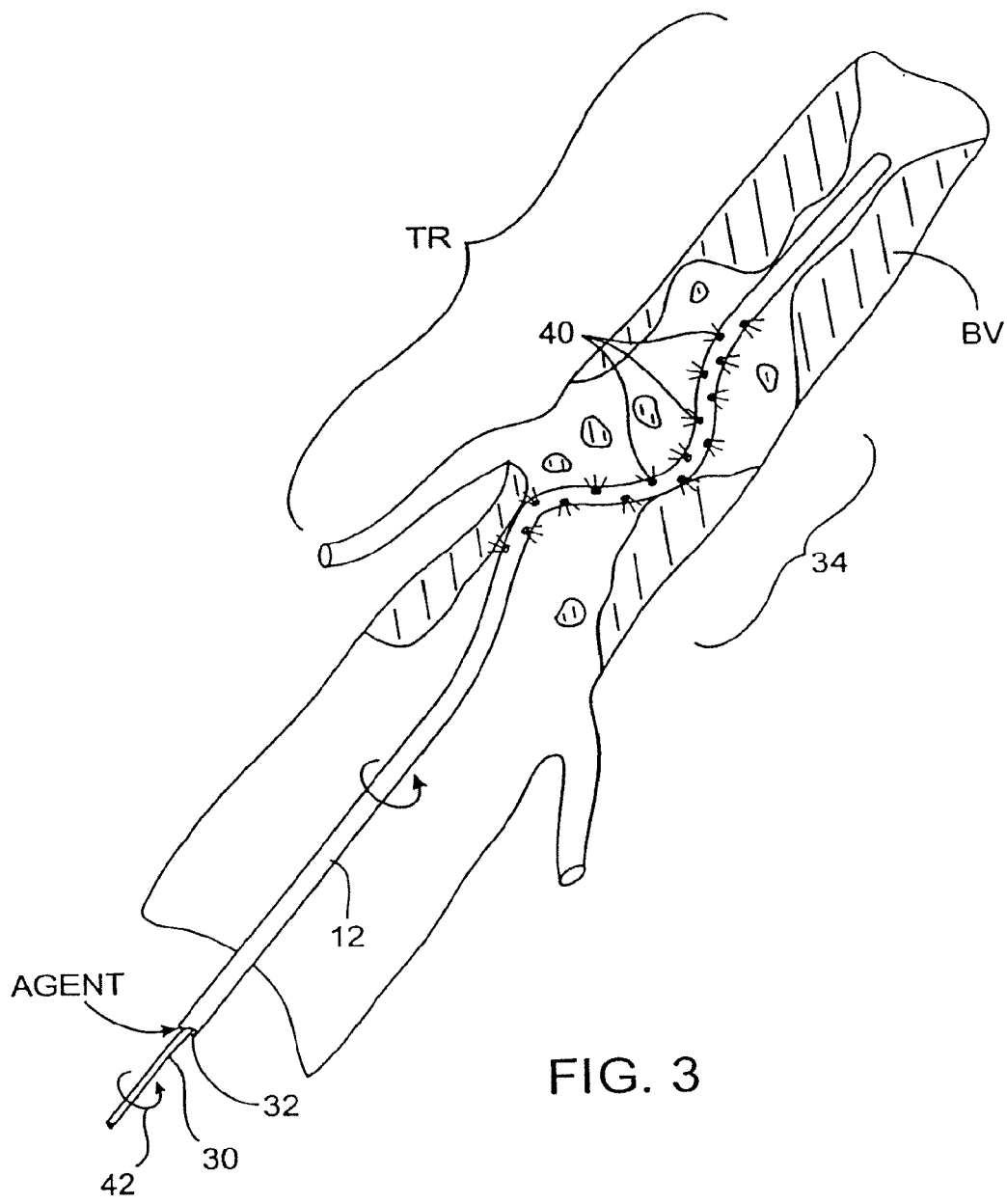
FIG. 3 illustrates use of the clot disruption apparatus of FIG. 1 in treating a thrombosed region within a blood vessel according to the methods of the present invention.

Use of the clot disruption apparatus 10 of FIGS. 1 and 2 is illustrated in FIG. 3. The non-linear region 34 of the catheter body 12 is positioned within a treatment region TR of the blood vessel BY being treated. Once in place, the agitator 30 is rotated, as indicated by arrow 42 and the non-linear region sweeps an ovoid volume within the treatment region TR, disrupting and dissolving clot as the thrombolytic agent is released from the ports 40. Alternatively or additionally, the non-linear region 34 could be rotated in the direction opposite to arrow 42, could be rotationally oscillated, axially oscillated, or combinations thereof.

Figure 4:
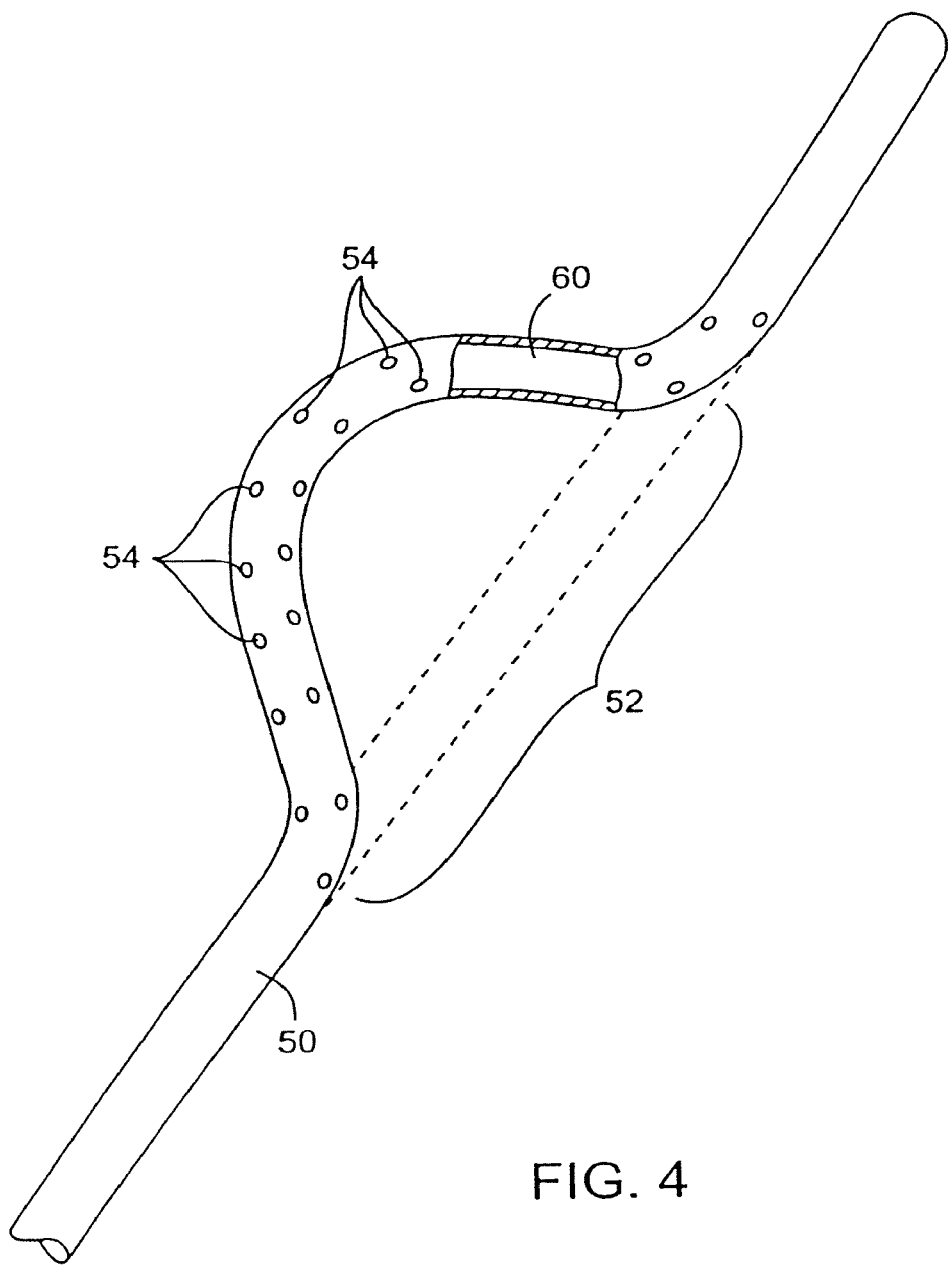
FIG. 4 illustrates an alternative construction of an agitator useful in the apparatus of the present invention.
Figure 5:
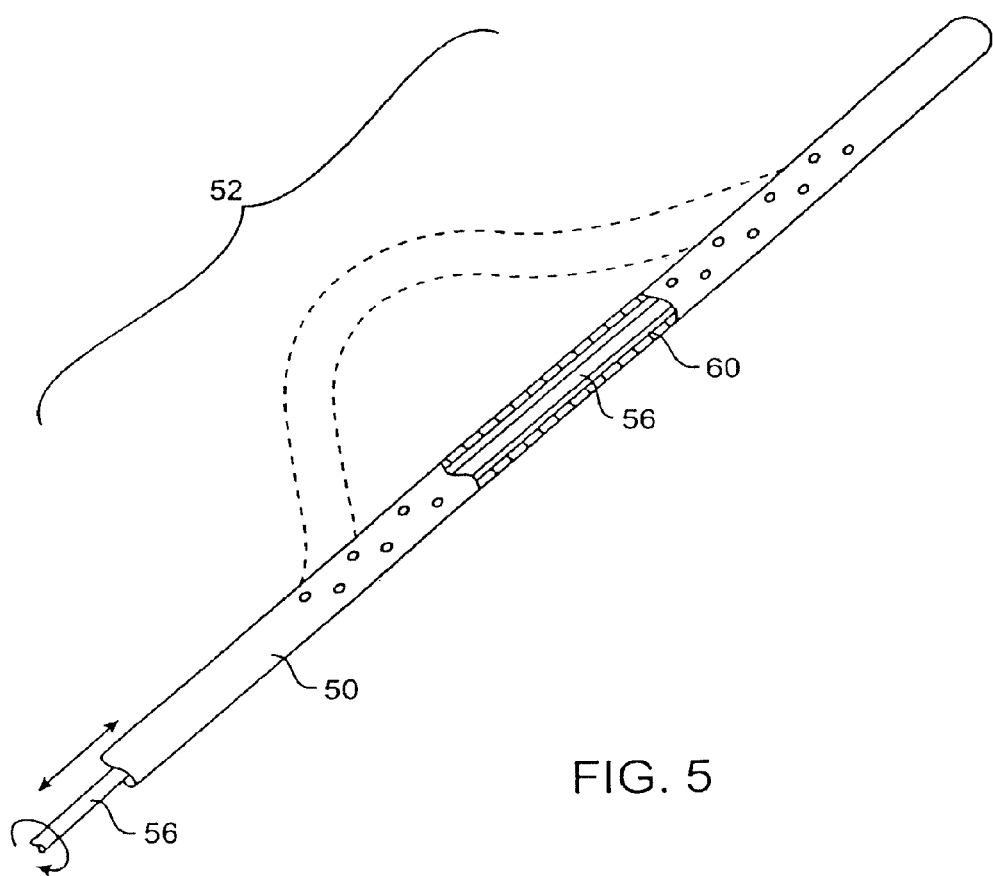
FIG. 5 illustrates a second alternative construction of an agitator useful in the apparatus of the present invention.

As described in the Summary above, the agitator may operate together with a thrombolytic agent delivery sheath (as illustrated in FIGS. 1-3) or may alternatively be configured to deliver the thrombolytic agent directly, e.g., through a lumen in the agitator as illustrated in FIG. 4. Agitator 50 of FIG. 4 includes a non-linear region 52 which consists of a simple, two-dimensional curve which forms a hump in the agitator. The non-linear region has a plurality of thrombolytic agent delivery ports 54 formed over its length so that the nonlinear region 52 can release the thrombolytic agent directly into the thrombus being treated as the agitator is rotated. In a first instance, the agitator 50 may be formed from a resilient material with the non-linear curve being formed so that it assumes the curve when released from constraint. The agitator 50 could then be delivered to a target site within a blood vessel within a separate delivery sheath. When the agitator 50 is advanced from the sheath, it will assume the non-linear geometry illustrated in FIG. 4. Alternatively, as shown in FIG. 5, the sheath 50 can be delivered with an internal stiffener 56 which tensions the agitator so that the non-linear region 52 (shown in broken line) is straightened (shown in full line) when the stiffener 56 is axially advanced within the lumen 60 thereof. It will also be possible to configure the agitator 50 so that it assumes a straight configuration when free from axial tension and compression. When under compression, however, the agitator will be formed so that it will collapse and assume the non-linear configuration 52 shown in FIG. 4. The agitator 50 could also be formed from heat memory alloys which are straight at room temperature but which assume their non-linear configuration when introduced to the body temperature. By introducing such catheters in a cooled environment, e.g., while bathed in cooled saline, they can reach their target site in a straightened configuration and thereafter assume the non-linear configuration as they return to body temperature.

Figure 6:
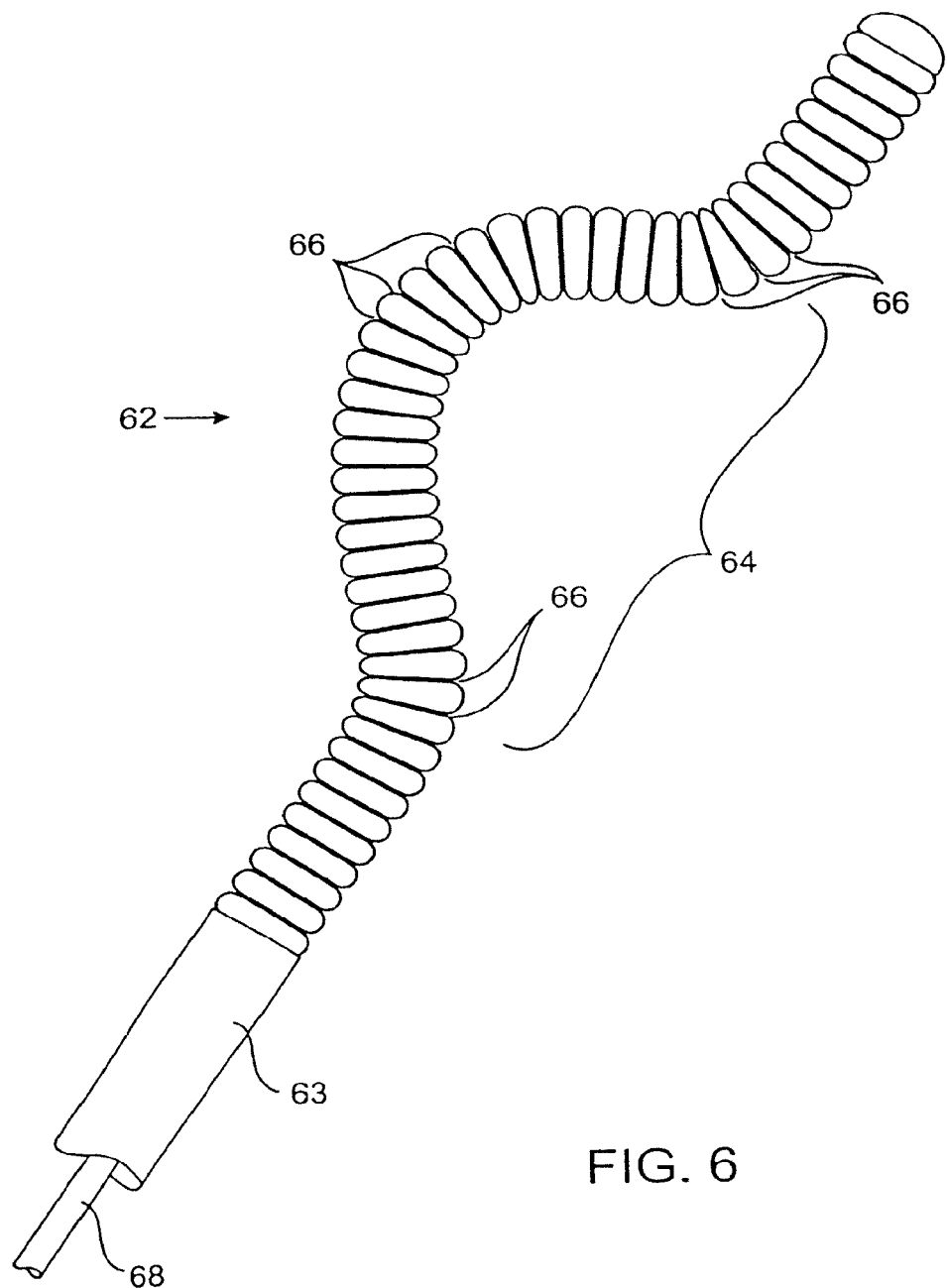
FIG. 6 illustrates a third alternative construction of an agitator useful in the apparatus of the present invention.

In addition to perforate structures for release of the thrombolytic agent, as shown in FIGS. 4 and 5, an agitator 62 having a sheath 63 formed as a coiled structure 64, as shown in FIG. 6, may also be used. The coil can be configured to have a non-linear region 64, such as a simple curve, or any of the other geometries discussed and illustrated above. When in a linear configuration, adjacent turns of the coil will lie close together and form a generally fluid-tight seal. When in the non-linear configuration illustrated in FIG. 6, however, adjacent turns of the coil will move apart to form a plurality of spaces or gaps 66 at regions where the coil structure turns. These gaps 66 connect to release the thrombolytic agent as the agitator is rotated. Sheath 63 may be induced into its linear configuration using a stiffening member 68, as illustrated.

Figure 7:
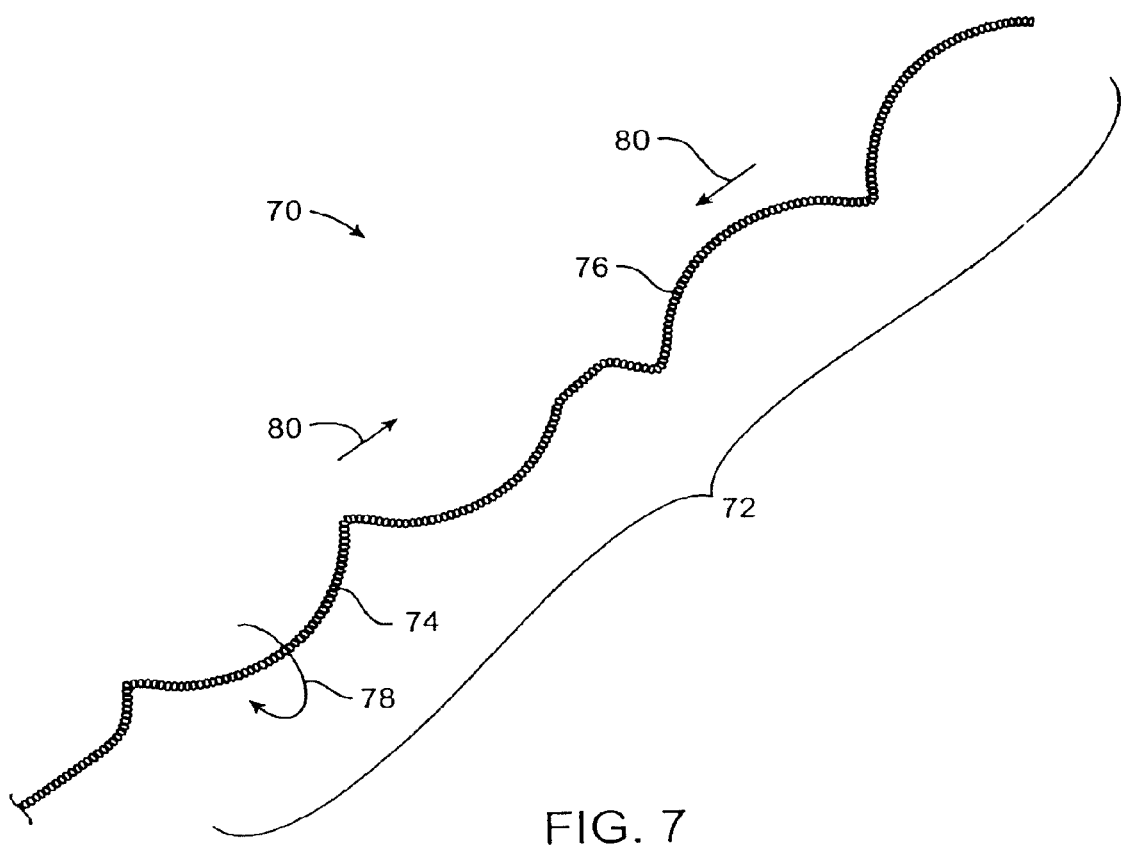
FIG. 7 illustrates a fourth configuration of an agitator useful in the apparatus of the present invention.

An agitator 70 having an alternating helical geometry is illustrated in FIG. 7. Non-linear region 72 of the agitator 70 comprises a first helical section 74 and a second helical section 76. The helical section 74 and 76 are wound in opposite directions so that when the agitator 70 is rotated in the direction of arrow 78, materials within the blood vessel lumen will be urged to move in the direction of arrows 80 toward a central region of the agitator 70. In this way, the agitator 70 creates its own isolation region within the blood vessel. The materials being disrupted and dissolved are constantly urged toward the center, to inhibit release from the treatment region. Over time, the materials will become completely broken down, or at least sufficiently broken down so that their release will not present significant risk to the patient.

Agitator 70 can comprise a sheath and separate agitator (similar to the design of FIGS. 1-3) or may comprise a monolithic structure where the thrombolytic agent is released directly through perforations or other discontinuities in the agitator wall. In some embodiments of the method, a simple bend in a guidewire may be used to mechanically agitate clot material and a therapeutic agent within an isolated region of the vessel, even using manual rotation of the guidewire.

Figure 8:
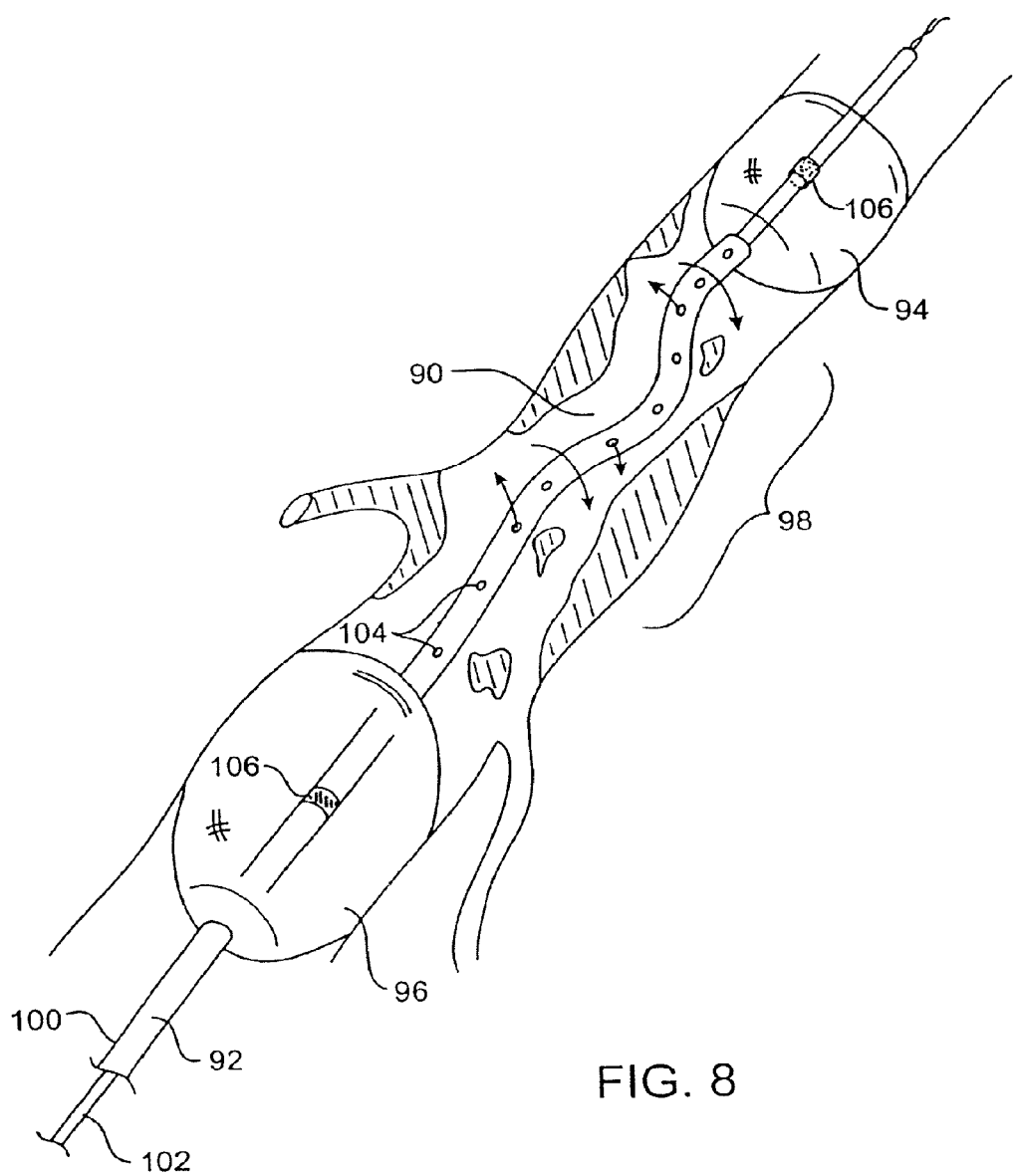
FIG. 8 illustrates a method and apparatus according to the present invention for treating an isolated region of the vasculature.

Referring now to FIG. 8, the clock disruption catheters of the present invention may be advantageously combined with balloon or other isolation means. Clot disruption catheter 90 comprises a catheter body 92 having a distal isolation balloon 94 and proximal isolation balloon 96 formed thereon. A non-linear region 98 of the catheter body 92 is formed between the isolation balloons 94 and 96. Conveniently, the isolation balloons 94 and 96 may be formed directly over a sheath 100 which remains stationary while an agitator 102 is rotated, oscillated, and/or axially translated therein. The balloons 94 and 96 may be inflated through a common or separate inflation lumens formed within the sheath 92. The inflation lumens (not shown) will be isolated from the thrombolytic agent delivery lumen. Thrombolytic agent is delivered through ports 104 formed in the sheath between the isolation balloons 94 and 96. Radiopaque markers 106 are positioned at either end of the treatment region, typically within the isolation balloons 94 and 96. The structure of catheter 90 is advantageous in that it will completely contain the thrombolytic agent and all disrupted clot between the isolation balloons 94 and 96. Optionally, aspiration means can be provided, e.g., through a fourth lumen within the sheath 100, in order to withdraw materials from the treatment region.

Figure 9:
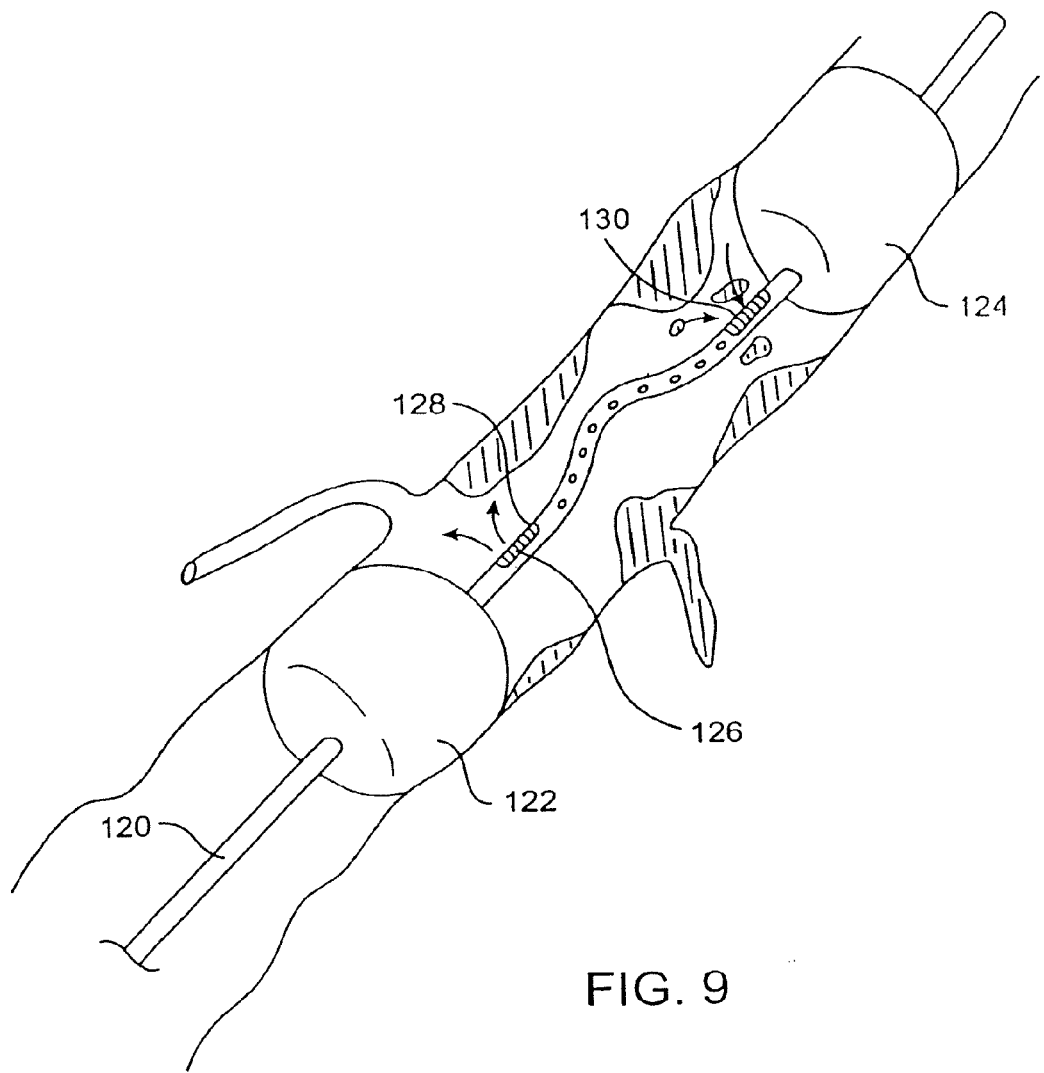
FIGS. 9, 9A and 9B illustrate alternative methods and apparatus according to the present invention for treating an isolated region of the vasculature.

Referring now to FIG. 9, a catheter 120 having means for recirculating the thrombolytic agent and other materials through a treatment region is illustrated. Catheter 120 comprises spaced-apart isolation balloons 122 and 124. The catheter is generally similar to that described above with reference to FIG. 8. Catheter 120, however, further includes a pump, typically in the form of an Archimedes screw 126 disposed between a first port 128 and a second port 130 on the body of catheter 120. Rotation of the Archimedes screw will draw material into the port 130 and expel the material from port 128. Such recirculation enhances the agitation and thrombolytic activity of the thrombolytic agent which is released through the ports as generally described above with respect to all earlier embodiments.

Figure 9A:
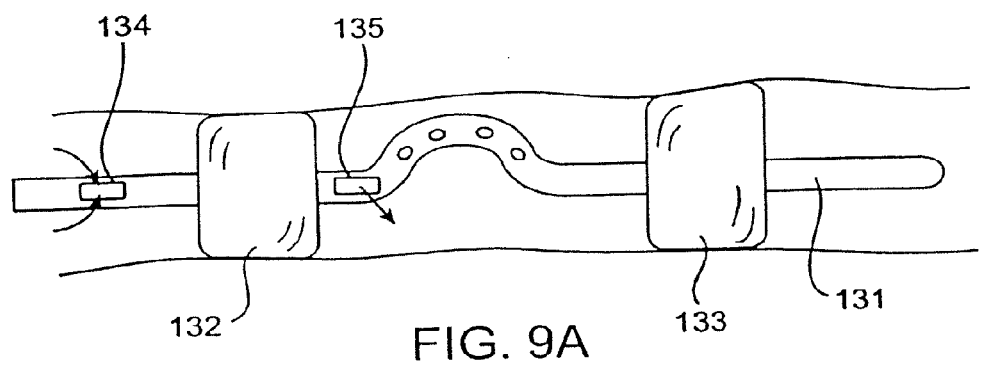

The catheters of the present invention can also be provided with blood bypass and perfusion lumens for a variety of purposes. For example, as illustrated in FIG. 9A, a catheter 131 having spaced-apart balloons 132 and 133 can have an inlet port upstream of proximal balloon 132 and an outlet port 135 between the balloons 132 and 133. In this way, fresh blood can be introduced into the otherwise isolated region between the balloons to enhance the thrombolytic activity of the tPA or other thrombolytic agent being released by the catheter.

Figure 9B:
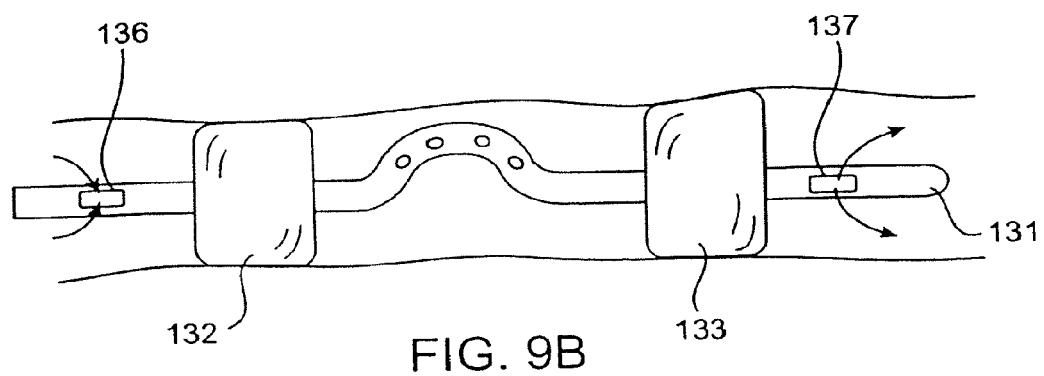

As illustrated in FIG. 9B, catheter 131 could also be provided with an inlet port 136 upstream of proximal balloon 132 and an outlet port 137 downstream of distal balloon 133 in order to provide perfusion downstream of the region being treated. In both FIGS. 9A and 9B, the inlet and outlet ports will be connected by internal lumen(s) which are preferably isolated from the lumen(s) which are supplying the thrombolytic agent.

Figure 10A:
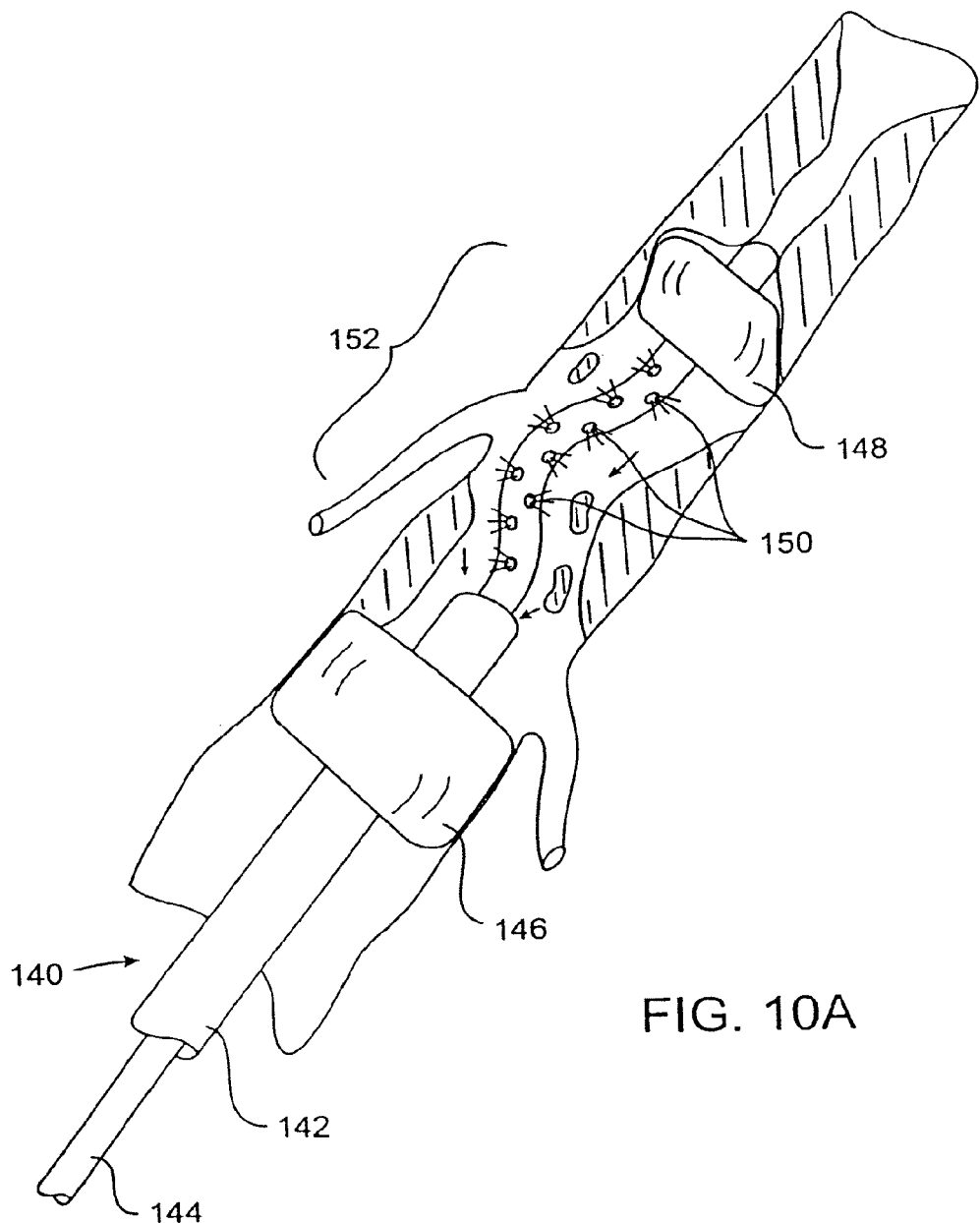
FIGS. 10A and 10B illustrate yet another alternative embodiment of the methods and apparatus of the present invention for treating an isolated region of the vasculature.
Figure 10B:
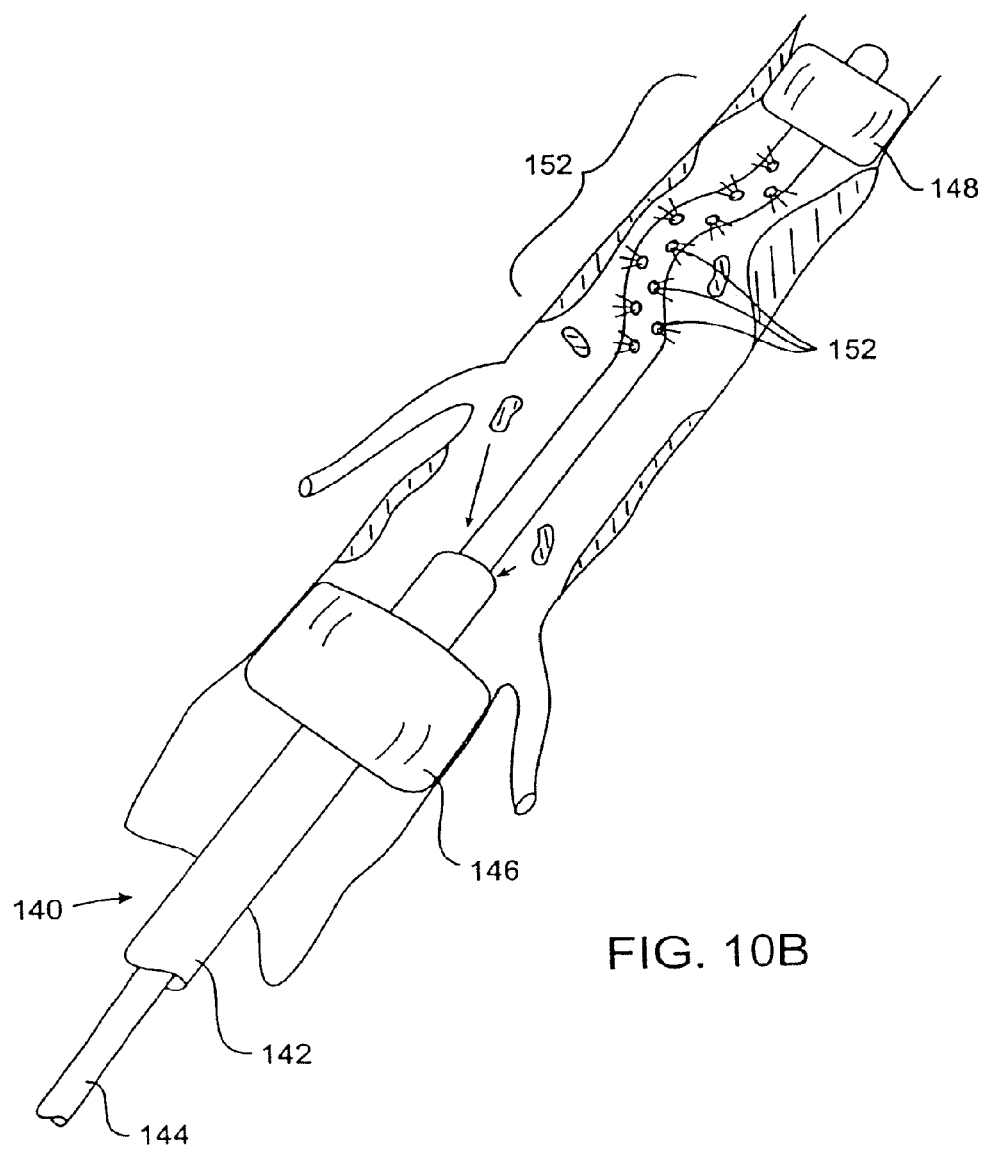

FIGS. 10A and 10B illustrate a catheter 140 comprising catheter body 142 and an inner catheter shaft 144. A proximal isolation balloon 146 is formed at the distal end of the catheter body 142. The distal isolation balloon 148 is formed at the distal end of the inner catheter body 144. Thrombolytic agent distribution ports 150 are formed over a non-linear region 152 of the inner catheter body 144. In this way, the length of the non-linear region and thrombolytic agent release region 152 can be adjusted by axially extending or retracting the inner catheter member 144 relative to the catheter body 142. In particular, balloon 146 on catheter body 142 may be anchored at a proximal end of a desired treatment region. The distal isolation balloon 148 may then be extended by a desired distance from the distal tip of the catheter body 142 to create an isolated treatment region therebetween (with both balloons being inflated). The non-linear region 152 may then be rotated with thrombolytic agent released in order to treat the clot and thrombus between the balloons. Optionally, the released emboli can be aspirated through the distal end of the catheter body 142 and withdrawn from the treatment region. After a first portion of the treatment region is remediated, the distal isolation balloon 148 can be deflated, and the distal end of the inner catheter member 144 extended further distally. This creates a new treatment region, which region can be treated in the manner just described, Two, three, or more such iterations can be performed successively in order to treat disseminated disease within a blood vessel lumen.

Figure 11:
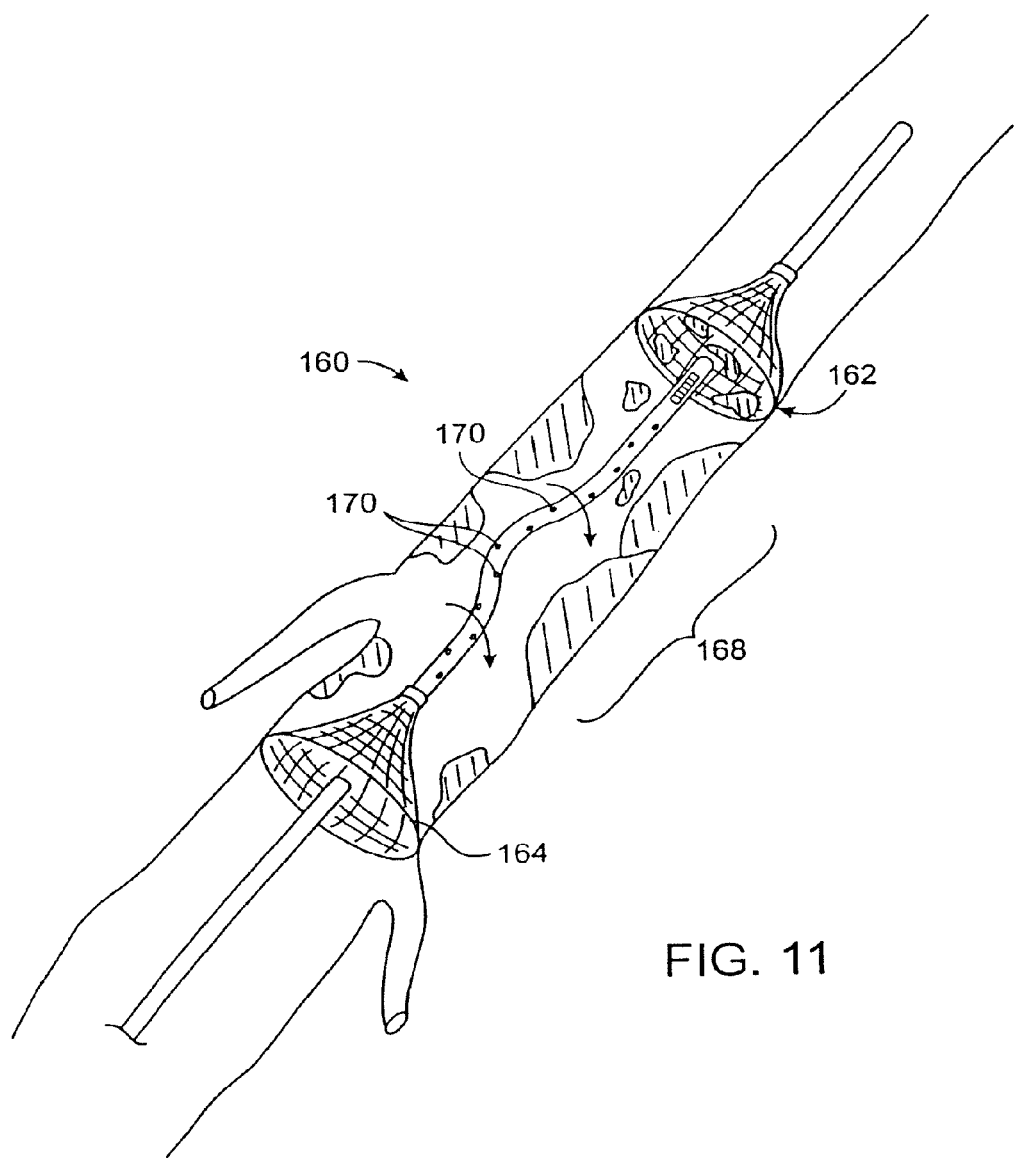
FIG. 11 illustrates a still further embodiment of the apparatus and methods of the present invention for treating an isolated region of the vasculature.

Referring now to FIG. 11, a clot disruption catheter 160 comprising expansible filter elements 162 and 164 is illustrated. The filter elements 162 and 164 provide partial isolation of a treatment region therebetween. The filter elements will capture emboli, but generally permit blood flow through the region. Catheter 160 further includes a non-linear region 168 and thrombolytic agent delivery ports 170, generally as described for previous embodiments. The non-linear region 168 may be rotated in order to effect clot disruption and dissolution, again generally as described above. Filter elements 162 and 164 will serve to capture at least most of the clot which is released.

Figure 12:
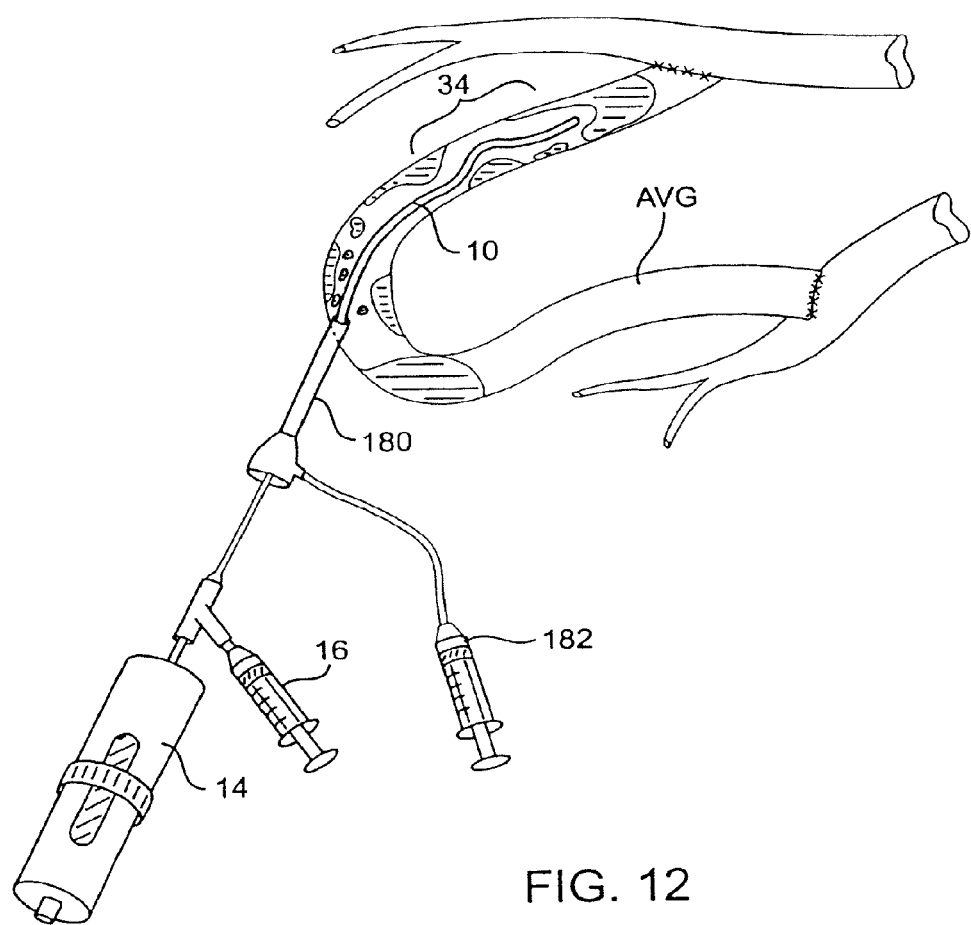
FIG. 12 illustrates a first method for treating an arteriovenous graft according to the methods of the present invention.

Referring now to FIG. 12, a clot disruption catheter, such as catheter 10 may be used to treat an arterio-venous graft AVG. The catheter 10 is introduced through a delivery sheath 180 so that non-linear region 34 lies within a highly thrombosed region of the graft AVG. The catheter is rotated and optionally axially translated, generally as described above. Thrombolytic agent can be released through the delivery device 16. The delivery sheath 180 can be adapted to provide for aspiration through a syringe 182 in order to retrieve at least a portion of the clot which is released from the graft.

Figure 13:
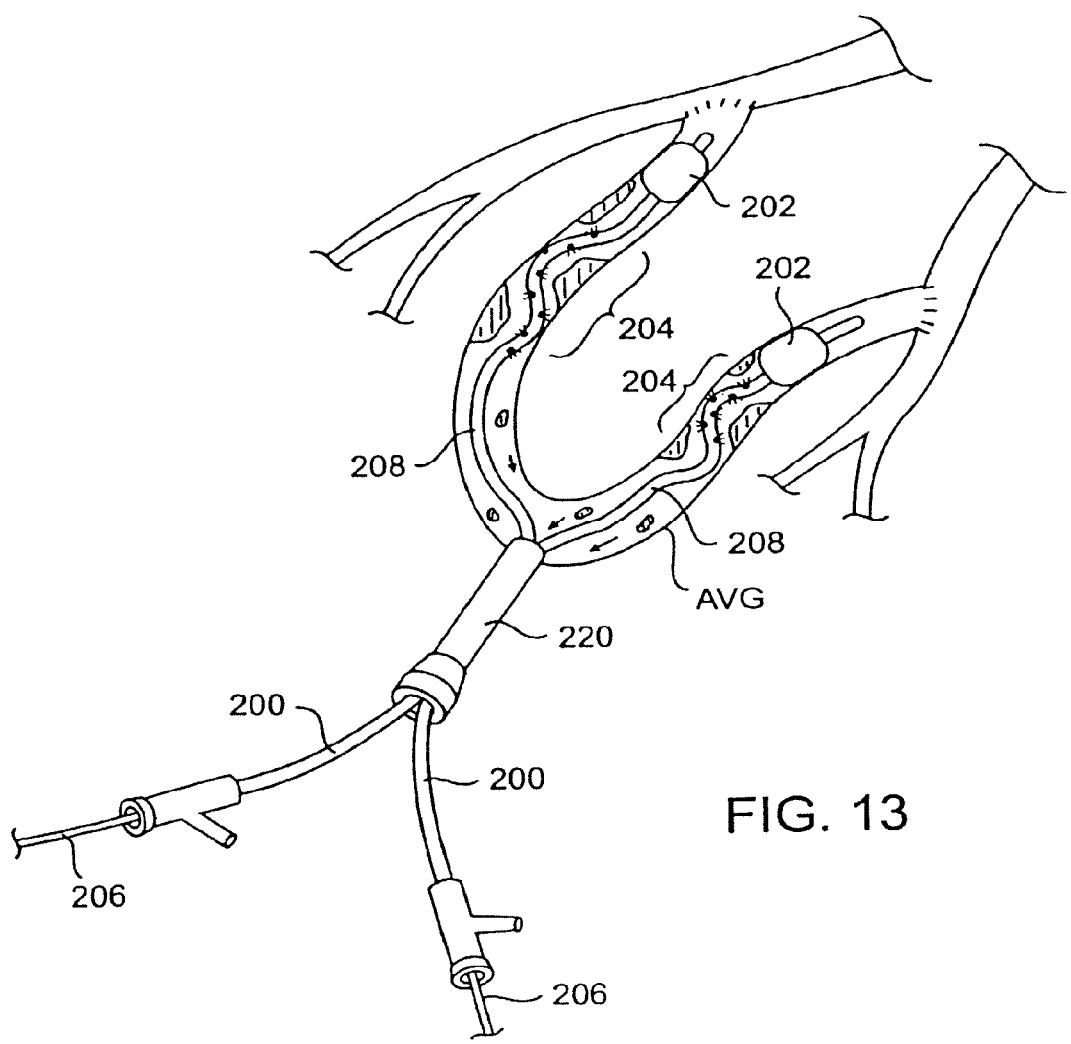
FIG. 13 illustrates a second method employing a pair of clot disruption catheters for treating an arterio-venous graft according to the methods of the present invention.

Two or more of the clot disruption catheters of the present invention may be used at the same time to treat a diseased region (or more than one diseased regions) within the patient. Referring to FIG. 13, an arterio-venous graft AVG can be treated with a pair of identical catheters 200, each of which includes a distal isolation balloon 202 but which does not include any proximal or other isolation balloons. Each catheter 200 further includes a non-linear region 204 defined by an agitator 206 within an exterior sheath 208. The AVG can be treated by positioning each distal isolation balloon 202 at a position close to the anastomotic junction with the associated artery and vein. The catheters 200 are introduced through a common delivery sheath 220, and the agitators 206 may be axially translated (repositioned) within the sheath in order to treat substantially the entire length between the distal isolation balloon 202 and the delivery sheath 220. Thrombolytic agent will be delivered generally as described above in other embodiments. Similarly, the non-linear regions 204 will be rotated in order to effect clot disruption and enhance thrombolytic agent activity. After treatment is completed, both catheters may be withdrawn through the sheath 220 and the AVG graft closed in the conventional manner.

Figure 14:
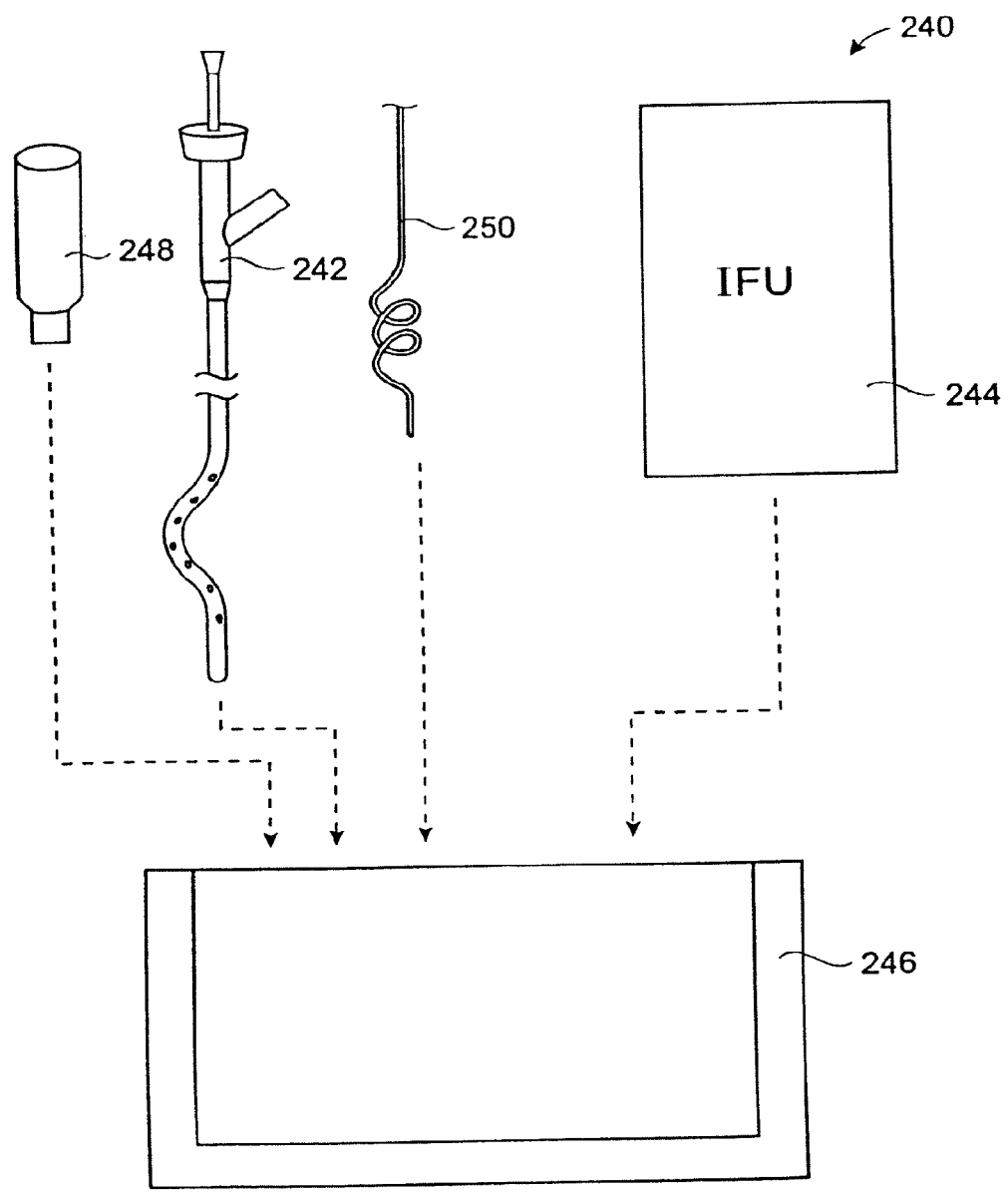
FIG. 14 illustrates a kit for performing the methods of the present invention, wherein the kit is constructed in accordance with the principles of the present invention.

The present invention still further comprises kits including at least some of the system components of the apparatus of the present invention described herein together with packaging, instructions for use, and/or other conventional kit components. For example, as illustrated in FIG. 14, a kit 240 may comprise at least a catheter 242, instructions for use 244, and packaging 246. The catheter 242 can be any of the catheters described hereinabove, and the instructions for use 244 may set forth any of the methods of the present invention described hereinabove. The catheter 242 will be packaged within the packaging 246, typically in a sterile fashion. Conventional medical device packaging may be used, such as a pouch, tube, tray, box, or the like. The instructions for use may be printed on a separate package insert, or may be printed in whole or in part on the packaging. Other kit components, such as a motor drive unit 248, an additional agitator 250 (optionally including two or more additional agitators having different geometries), may also be added.

Figure 15:
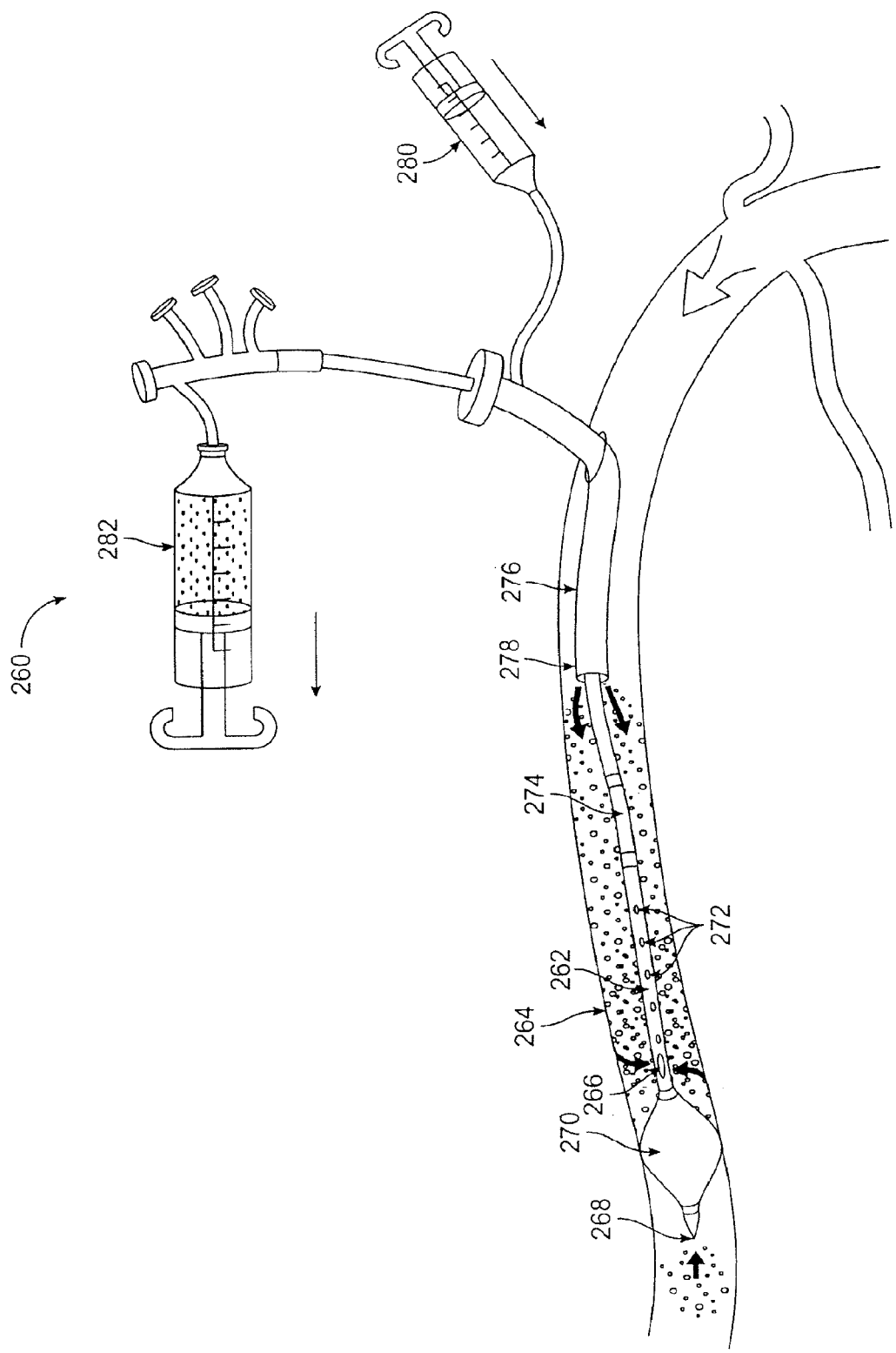
FIG. 15 illustrates a clot disruption apparatus having a sheath and a catheter body, the catheter body having a lumen with a distal-end opening and a side opening according to one embodiment of the present invention.

Referring now to FIG. 15, another embodiment of a clot disruption apparatus 260 suitably includes a catheter body 262 having a proximal end, a distal end, and at least one lumen (not visible in FIG. 15). The lumen has at least one side opening 266 and a distal-end opening 268, both at or near the distal end of catheter body 262. Catheter body 262 typically further includes a first radially expandable body 270. Optionally, in various embodiments, catheter body 262 may further include a flow resistor (not shown), a second radially expandable body 274 and/or a plurality of spaced-apart smaller openings 272 into the lumen. Apparatus 260 may optionally further include a sheath 276 with a luminal opening 278 for infusing and/or aspirating fluids, an aspiration mechanism 282 and/or an infusion mechanism 280. Although not shown in FIG. 15, apparatus 260 is typically positioned within a luminal length of a blood vessel 264 by passing apparatus 260 over a guidewire. In some embodiments, a guidewire is included as part of apparatus 260 or as part of a kit including apparatus 260. Apparatus 260 may optionally further include one or more of the elements described with reference to various embodiments set forth above, such as a mechanical agitator, an aspiration device, and/or the like.

Generally, as described in detail above, clot disruption apparatus 260 will be positioned in a luminal length of blood vessel 264 such that one or more agents may be infused at an area of clot. Optionally, agitating means may be used to agitate the clot and aspiration means may be used to aspirate clot and/or fluid containing clot particles, blood, infusate and the like. In one embodiment, infusion is performed through sheath 276 and aspiration is performed through side opening 266 and distal-end opening 268 of the lumen of catheter body 262. Such functionality is designated by the hollow arrows (infusion) and the dark arrows (aspiration) in FIG. 15. Conversely, infusion may alternatively be performed through side opening 266 and distal end opening 268 and aspiration may be performed through sheath 276. In another embodiment, aspiration and/or infusion may additionally occur through spaced-apart openings 272. In one embodiment, infusion and aspiration are performed simultaneously, while in others infusion occurs before aspiration. Again in various embodiments, infusion and/or aspiration may be performed with first radially expandable body 270 expanded, with second radially expandable body 274 expanded, with neither expanded, or in some cases with both expanded.

In other embodiments of the present invention, described in further detail below, apparatus 260 does not include a similar sheath 276. In some of these embodiments, infusion, aspiration and passage of a guidewire are all performed through a common lument in catheter body 262. In other embodiments, separate lumens in catheter body 262 are used for separate functions, for example one lumen may be for infusion and another lumen may be for aspiration and passage of a guidewire. Alternatively, one lumen may be used for infusion and guidewire passage and another may be used for aspiration. In various of these embodiments, infusion, aspiration or both may be performed with a guidewire in place within apparatus 260, for example with a guidewire tip protruding through distal-end opening 268.

Generally, apparatus 260 enables fluid flow, as in aspiration and/or infusion, to occur preferentially through the at least one side opening 266 while still allowing minimal aspiration and/or infusion through distal-end opening 268. Such preferential fluid flow is accomplished through any of a number of suitable means. In many embodiments, for example, the cross-sectional area of distal-end opening 268 is significantly smaller than the cross-sectional area of at least one side opening 266. For instance, in one embodiment the cross-sectional area of distal-end opening 268 is between about 0.1% and about 20%, and more preferably between about 1% and about 5%, of the cross-sectional area of at least one side opening 266. In various embodiments, this difference in cross-sectional area will be sufficient to provide preferential fluid flow through at least one side opening 266.

In other embodiments, apparatus 260 further includes a flow resistor (not shown in FIG. 15) between at least one side opening 266 and distal end opening 268 for resisting fluid flow through at least one lumen in catheter body 262. Flow resistor typically acts in conjunction with a difference in cross-sectional areas between distal-end opening 268 and at least one side opening 266 to provide preferential, or predominant, fluid flow through at least one side opening 266.

Referring now to FIG. 16a, one embodiment of a clot disruption apparatus distal end 300 suitably includes a catheter body 302 having a lumen 304, a flow resistor 310 and a first expandable body 314. Lumen 304 further includes a side opening 306 and a distal-end opening 308, and flow resistor 310 is configured generally as a cylindrical member having a cylindrical channel 312. In other embodiments, flow resistor 310 may have any other suitable configuration, as will be described more fully below. In one embodiment, for example, flow resistor 310 may comprise a membrane, disc or the like, having one or more holes, rather than a cylinder having a channel. In other embodiments, as described above, distal end 300 does not include a flow resistor.

Generally, distal-end opening 308 will have a significantly smaller cross-sectional area than side opening 306. For example, in one embodiment the cross-sectional area of distal-end opening 308 is between about 0.1% and about 20%, and more preferably between about 1% and about 5%, of the cross-sectional area of side opening 306. In embodiments of distal end 300 including flow resistor 310, channel 312 will typically have a cross-sectional area smaller than distal-end opening. For example, in one embodiment, cross-sectional area of channel 312 is between about 0.1% and about 8%, and more preferably between about 0.5% and about 4%, of the cross-sectional area of side opening 306. In other embodiments, the cross-section area of channel 312 may be approximately equal to the cross-sectional area of distal-end opening 308. In embodiments including a membranous or disc-shaped flow resistor, a hole or holes through the membrane or disk will have cross-sectional areas similar to those just described in relation to cylindrical flow resistor 310 and channel 312.

Channel 312 (or channels, or holes, or the like) may have any suitable diameter, configuration or shape for allowing the passage of a guidewire through flow resistor 310. Channel 312 also typically allows passage of some fluid through flow resistor 310. In some embodiments, minimal fluid flow may occur with a guidewire in place in channel 312. Flow resistor 310 does resist flow through lumen 304, however, thus assisting in the provision of preferential fluid flow through at least one side opening 306 relative to distal-end opening 308. In one embodiment, the percentage of total fluid flow through flow resistor 310 and distal-end opening 308 is between about 0.1% and about 20% of the total fluid flow through lumen 304, with the remaining about 80% to about 99.9% flowing through side opening 306. More preferably, the percentage of total fluid flow through flow resistor 310 and distal-end opening 308 is between about 1% and 5% of the total fluid, with the remaining about 95% to about 99% flowing through at least one side opening 306.

Flow resistor 310 may be made of any suitable material and may have any suitable configuration for allowing passage of a guidewire and for inhibiting fluid flow. In some embodiments, flow resistor 310 is made of a compliant, silicon-based material. Other materials may be used, however, such as but not limited to plastic, metal, polymer, or a combination thereof. Similarly, flow resistor 310 may have any suitable length, shape, diameter or configuration. In most embodiments, the outer diameter of flow resistor 310 will be approximately equal to the inner diameter of lumen 304, to enhance flow inhibition. Since many diameters of catheter bodies, lumens and the like are contemplated within the scope of the present invention, many possible diameters of flow resistor 310 are also contemplated.

Referring now to FIGS. 16b-d, flow resistor 310 (shown in front view) may suitably include multiple channels, openings, slits, pores, holes apertures, and/or the like, for allowing passage of a guidewire and/or inhibiting fluid flow. In the embodiment shown in FIG. 16b, for example, flow resistor 310 includes a guidewire channel 326 and a fluid channel 328. Such a configuration may be advantageous, for example, when infusion or aspiration is desired with a guidewire in place to support or position catheter body 302. FIG. 16c shows another embodiment, in which flow resistor 310 includes a guidewire channel 324 and multiple fluid channels 322. Of course, in either of the embodiments in FIGS. 16b and 16c, if a guidewire is not in place within the guidewire channel, fluid may flow through the guidewire channel. In some embodiments, as mentioned above, some fluid flow may occur through a channel even when a guidewire is in place in the channel.

Referring now to FIG. 16d, yet another embodiment of flow resistor 310 includes multiple slits 320 for allowing passage of a guidewire. Slits 320 typically have some amount of flexibility, to allow passage of the guidewire. In some embodiments, slits 320 do not allow passage of fluid, while in other embodiments fluid may pass through slits 320. In other embodiments, slits 320 may be combined with one or more channels to allow fluid flow. In still other embodiments, slits may be configured to permit fluid flow in one direction but not another—i.e., they may operate as a one-way valve.

Figure 17:
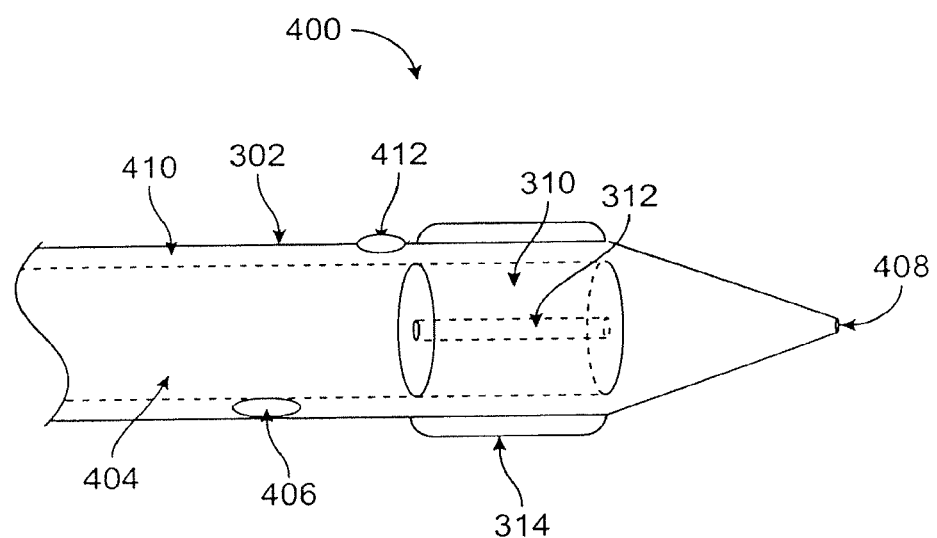
FIG. 17 illustrates a cross section of the distal end of a clot disruption apparatus having a cylindrical flow resistor and two separate lumens, one for infusion and one for aspiration, according to one embodiment of the present invention.

Referring now to FIG. 17, another embodiment of a clot disruption apparatus distal end 400 suitably includes a catheter body 302 having an infusion lumen 404 and an aspiration lumen 410, a first expandable body 314 and a flow resistor 310 with a channel 312. In this embodiment, aspiration lumen 410 includes an aspiration opening 412 and infusion lumen 404 includes a side opening 406 and a distal-end opening 408.

In an embodiment as in FIG. 17, infusion is performed via infusion lumen 404 side opening 406 and distal-end opening 408 and aspiration is performed via aspiration lumen 410 and aspiration opening 412. Guidewire passage occurs through infusion lumen 404. Due to its positioning within infusion lumen 404, flow resistor 310 inhibits flow only during infusion. In an alternative embodiment, the functionality of the lumens and openings shown in FIG. 17 may be switched, such that aspiration occurs via infusion lumen 404 and infusion side opening 406 and distal-end opening 408, and infusion occurs via aspiration lumen 410 and aspiration opening 412. In that embodiment, flow resistor 310 inhibits flow during infusion and not during aspiration. Other embodiments are contemplated, for example in which flow resistor 310 inhibits flow in more than one lumen, in which no flow resistor is used, and the like. Generally, any suitable configuration of a clot disruption apparatus distal end for providing preferential or predominant fluid flow from at least one side opening relative to a distal-end opening is contemplated within the scope of the invention.

Figure 18A:
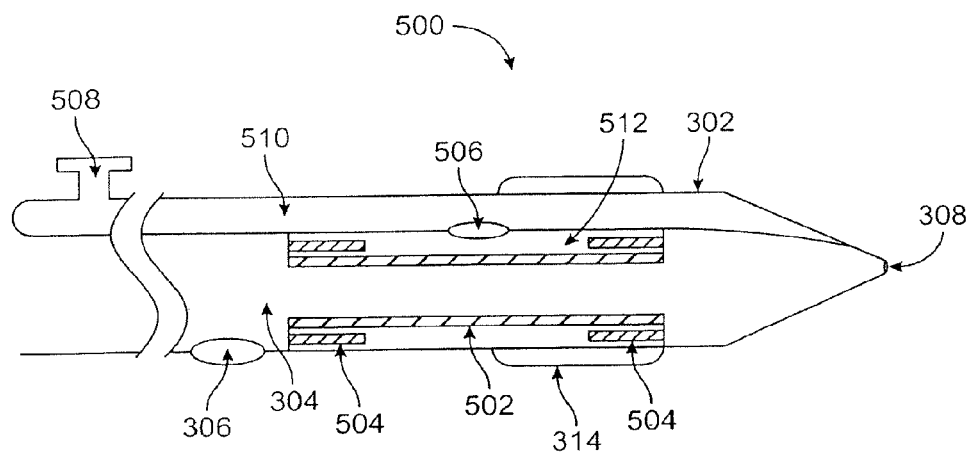
FIGS. 18a-b illustrate a cross section of the distal end of a clot disruption apparatus having a compliant membrane flow resistor and a common lumen for infusion and aspiration, according to one embodiment of the present invention.
Figure 18B:
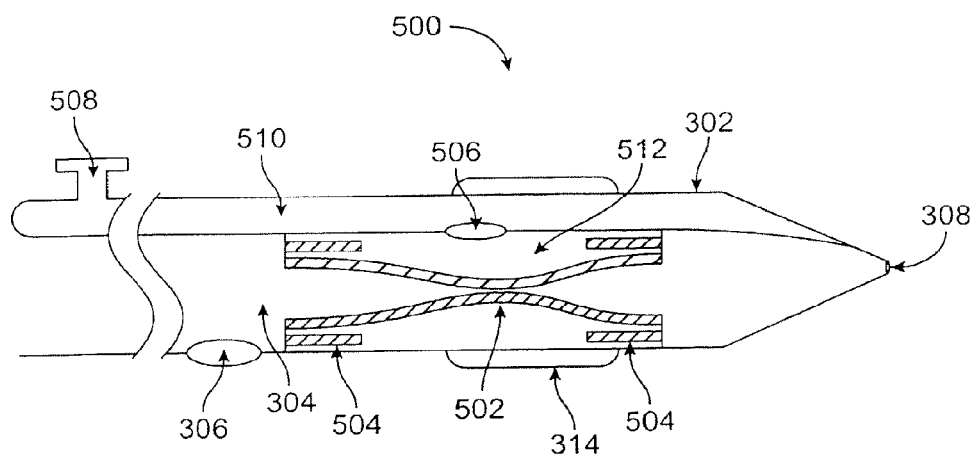

Referring now to FIGS. 18a and 18b, another embodiment of a clot disruption apparatus distal end 500 suitably includes a catheter body 302 having an infusion/aspiration lumen 304, a flow resistor 512, and a first expandable body 314. In this embodiment, catheter body 302 further includes a flow resistor infusion lumen 510 and a flow resistor infusion opening 506 and the clot disruption apparatus includes a flow resistor infusion port 508 at a proximal location. Infusion/aspiration lumen 304 further includes a side opening 306 and a distal-end opening 308. Flow resistor 310 comprises a compliant membrane 502 and an attachment mechanism 504.

Generally, in an embodiment as in FIGS. 18a and 18b, when it is desired to inhibit flow through distal-end opening 308 using flow resistor 310, an infusate may be infused into flow resistor infusion port 508, through flow resistor infusion lumen 510 and flow resistor infusion opening 506, to pressurize and thus move compliant membrane 502. Compliant membrane 502 is typically attached to an inner surface of infusion/aspiration lumen 304 by any suitable attachment mechanism 504 or adhesive device. When flow inhibition is no longer desired, infusate in flow resistor 512 maybe discharged or otherwise released, to allow compliant membrane to assume its original shape. In various embodiments and configurations, compliant membrane 502 and flow resistor 512 in general may be configured to allow no passage of fluid, some passage of fluid, and/or passage of a guidewire.

Figure 19:
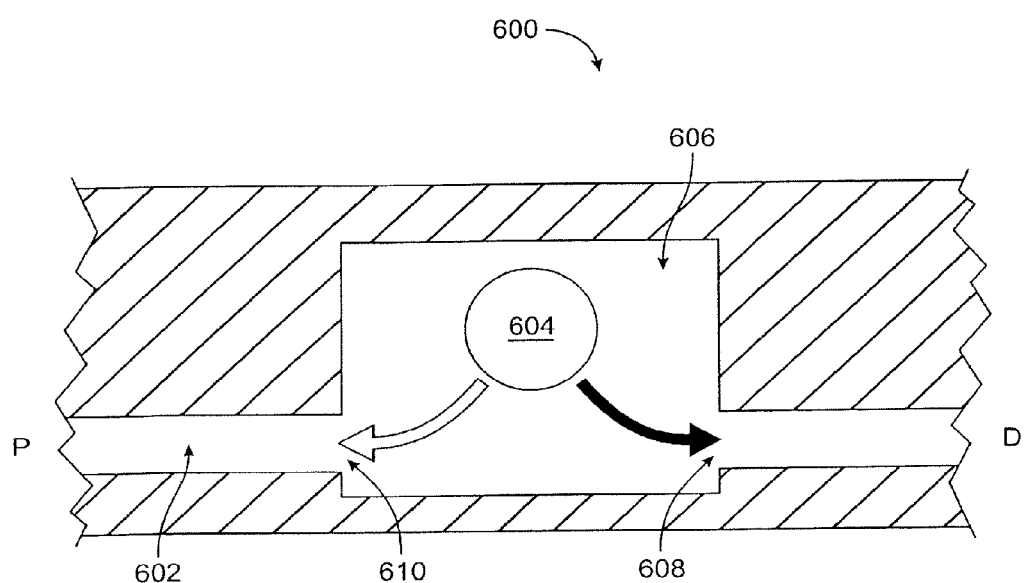
FIG. 19 illustrates a cross section of a ball valve flow resistor which may be used in the distal end of a catheter body lumen according to one embodiment of the present invention.

Referring now to FIG. 19, yet another embodiment of a flow resistor 600 may comprise a ball valve. Such a valve suitably includes a ball 604, a channel 602, a valve entrance 610, a valve exit 608, and a side housing 606. In one embodiment, when a guidewire (not shown) is inserted through channel 602, the guidewire moves ball 604 to a position within side housing 606. When the guidewire is not within channel 602, ball 604 is free to move anywhere within the valve. During infusion of fluid from proximal (P) to distal (D), ball 604 will naturally be moved by the fluid to a position adjacent valve exit 608, as shown by the darkened arrow, and will partially or wholly block fluid flow through valve exit 608. During aspiration of fluid from D to P, ball 604 will naturally be moved by the fluid to a position adjacent valve entrance 610, as shown by the hollow arrow, and will partially or wholly block fluid flow through valve entrance 610.

Referring now to FIGS. 20a-g, one embodiment of a method for disrupting clot according to the present invention is shown. Many various methods according to the present invention may be used for disrupting clot. For example, various steps may be added to or deleted from the process shown in FIGS. 20a-g, various additional apparatus may be used, different apparatus may be substituted, the order of steps may be changed and/or the like, without departing from the scope of the present invention. Therefore, the exemplary methods described in FIGS. 20a-g and FIGS. 21a-g are provided for exemplary purposes only and should not limit the scope of the invention.

Figure 20A:
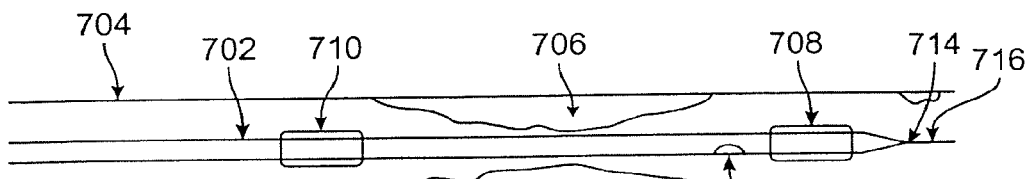
FIGS. 20a-g illustrate a method for disrupting a clot according to one embodiment of the present invention.

That being said, with reference to FIG. 20a, a first step in a method for clot disruption includes positioning a catheter body 702 within a blood vessel 706 at the site of a clot 706. Catheter body 702 includes a distal balloon 708, a proximal balloon 710, a side opening 712, and a distal-end opening 714. Typically, catheter body 702 will be positioned within blood vessel 704 by passing body 702 along a guidewire 716.

Figure 20B:
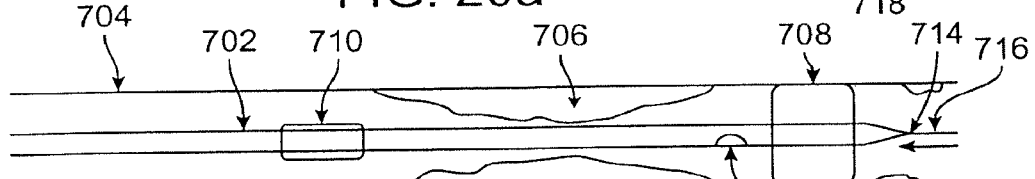

In a next step, as in FIG. 20b, distal balloon 708 is inflated and guidewire 716 removed. From catheter body 702, as designated by the proximal-pointing arrow. In other embodiments, methods include leaving a guidewire in place during infusion, clot disruption, and/or aspiration. As described above, various embodiments provide minimal fluid flow through distal-end opening 714 with a guidewire in place, while other embodiments provide for no flow through distal-end opening 714 with the guidewire in place.

Figure 20C:
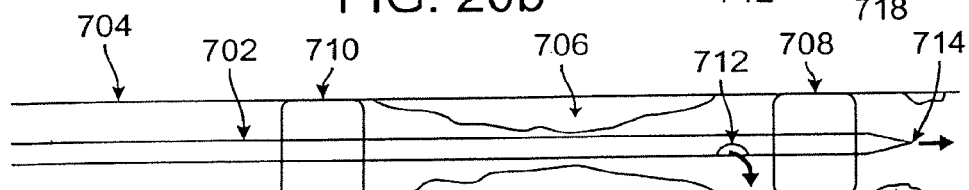

Next, as in FIG. 20c, proximal balloon 710 is inflated and an agent to enhance clot disruption, such as a thrombolytic agent, is infused through side opening 712 and distal-end opening 714 (designated by arrows). In some embodiments, infusion may begin before inflating proximal balloon 710. In other embodiments, infusion, clot disruption and aspiration may all be performed without inflating proximal balloon 710. Alternatively, infusion may commence concurrently with proximal balloon 710 inflation. Generally, as described in detail above, infusion is performed preferentially through side opening 712, relative to distal-end opening This may be accomplished by providing a distal-end opening 714 with a smaller cross-sectional area than side opening 712, by providing a flow resistor within catheter body 702, or by a combination of the two.

Figure 20D:
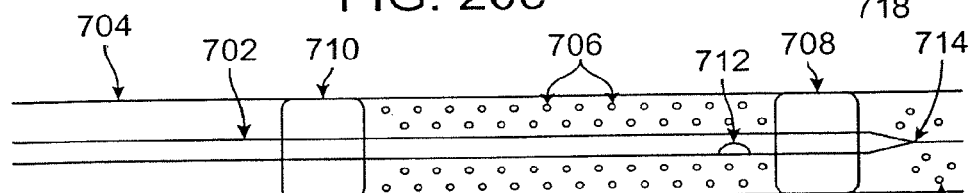

In FIG. 20d, with the assistance of the infused agent, clot 706 begins to disrupt or dissolve. Additionally, because some infusion occurs through distal-end opening 714, secondary clot 718 distal to distal balloon 708 is also disrupted/dissolved. Generally, the majority of the infused agent, which was distributed through side opening 712, is held within the blood vessel 704 in an area between proximal balloon 710 and distal balloon 708. Containment of the infused substance largely within this area serves to enhance the clot disruption process and to prevent side effects which may occur from systemic distribution of the agent.

Figure 20E:
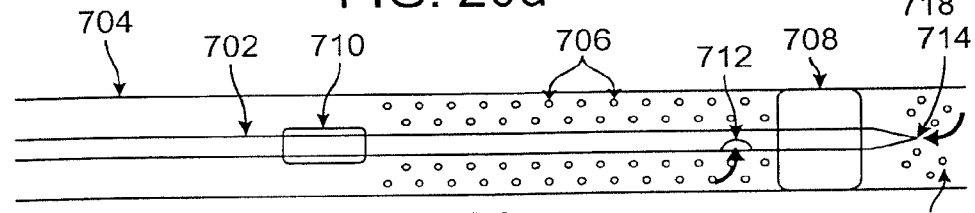

Next, in FIG. 20e, proximal balloon 710 is deflated and aspiration of blood, disrupted clot 706, infused agent, and disrupted secondary clot 718 commences. Again due to the relative cross-sectional areas of side opening 712 and distal-end opening, due to the presence of a flow resistor, or both, aspiration occurs preferentially or predominantly through side opening 712. In other embodiments, aspiration may occur through a separate lumen with one or more separate openings. Also alternatively, aspiration may begin before proximal balloon 710 is deflated or while proximal balloon 710 is deflating.

Figure 20F:
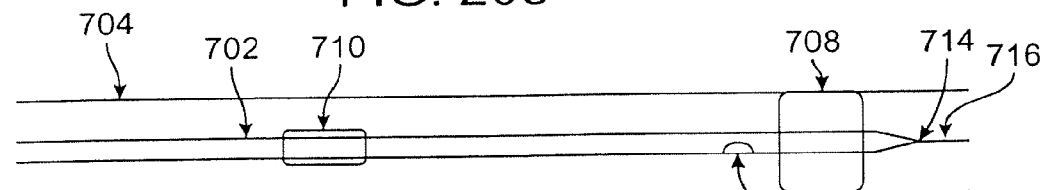
Figure 20G:
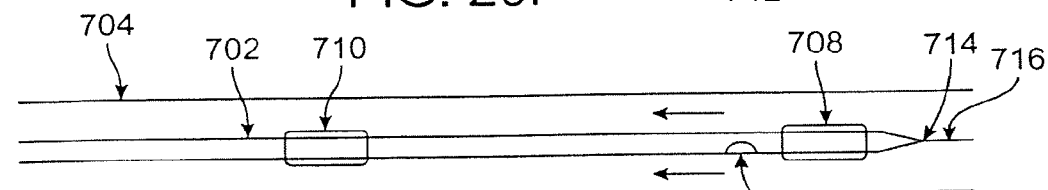

In FIG. 20f, disrupted and dissolved clot has been aspirated from blood vessel 704 and guidewire 716 has been repositioned in catheter body 702, through distal-end opening 714. Finally, in FIG. 20g, catheter body 702 is beginning to be removed from blood vessel 704, by passing catheter body 702 proximally over guidewire 716 (designated by proximally directed arrows). Guidewire 716 is then removed from blood vessel 704 (not shown).

Referring now to FIGS. 21a-g, another embodiment of a method for disrupting clot is shown. The method first includes positioning a catheter body 802 in a blood vessel 804 at a location for disrupting clot 806 by passing catheter body 802 over a guidewire 816. The catheter body 802 suitably includes a distal balloon 808, a side opening 812 and a distal-end opening 814 communicating with a first lumen (not visible), and second side opening 820 communicating with a second lumen (not visible).

Next, in FIG. 20b, distal balloon 808 is inflated when catheter body 802 has been positioned in a desired location within blood vessel 804. Guidewire 816 is left in place within catheter body 802, the distal end of guidewire 816 protruding from distal-end opening 814. As in FIG. 21c, an agent is then infused preferentially from side opening 812, with a small amount of fluid flowing or dripping from distal-end opening 814 (designated by arrows). This small amount of agent/fluid may help dissolve smaller, secondary clot 818 distal to distal balloon 808 into harmless particles or dissolved material.

In FIG. 21d, clot 806 and secondary clot 818 have been disrupted by the agent. In FIG. 21e, clot 806, blood and/or agent is aspirated by second opening 820 and second lumen. When a desired amount of disrupted clot 806 is aspirated, as in FIG. 2 If, distal balloon 808 is deflated. Finally, as in FIG. 21g, catheter body 802 is withdrawn from blood vessel 804 over guidewire 816. Guidewire 816 may then be removed from blood vessel 804 (not shown). As previously mentioned, FIGS. 21a-g describe only one embodiment of a method of the present invention, and many additional embodiments are contemplated. For example, aspiration and infusion may occur through the opposite lumens from those shown in FIGS. 21a-g. Alternatively, guidewire 816 may be removed during a portion of the procedure. These and/or other changes may be made without departing from the scope of the present invention.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for disrupting a clot over a luminal length of a blood vessel, the method comprising:

positioning a catheter body in the luminal length of the blood vessel, the catheter body comprising a proximal end, a distal portion having at least one lumen allowing passage of a wire or agitator, the distal portion of the catheter body having at least one port formed therein so as to permit fluid flow from the lumen;

actuating an agitator disposed within the catheter body for mechanical disruption of a clot in the blood vessel, the agitator comprising a non-linear region disposed in the catheter body lumen such that the at least one port is positioned along a distal portion of the non-linear region;

infusing a fluid comprising a thrombolytic agent through the lumen of the catheter body such that the fluid passes through the at least one port of the distal portion positioned along the distal portion of the non-linear region and into the luminal length of the blood vessel.

2. The method of claim 1, wherein positioning the catheter body comprises passing the catheter body over a guidewire or agitator.

3. The method of claim 1, wherein the non-linear region of the agitator is disposed in the lumen such that the fluid is infused both about the non-linear region and distal to the non-linear region.

4. The method of claim 3, wherein the catheter body comprises a plurality of ports formed along a length of the body and one or more ports of the plurality are positioned distal to the non-linear region.

5. The method of claim 4, wherein at least two ports of the plurality have different cross-sectional areas.

6. The method of claim 5, wherein the plurality of ports are formed such that fluid infusion occurs substantially evenly along the length of the body.

7. The method of claim 1, wherein the agitator is resilient and radially expandable so as to be constrained by the blood vessel as it is rotated.

8. The method of claim 1, wherein the blood vessel is a vein.

9. The method of claim 1, wherein the blood vessel is an artery.

10. The method of claim 1, further comprising isolating at least a portion or end of the luminal length of the blood vessel.

11. The method of claim 10, further comprising isolating both a proximal end and a distal end of the luminal length.

12. The method of claim 10, wherein isolating comprises expanding at least one occlusion balloon.

13. The method of claim 1, further comprising aspirating fluid or clot material from the blood vessel.

* * * * *